United States Patent [19]
Bendele et al.

[11] Patent Number: 5,416,090
[45] Date of Patent: May 16, 1995

[54] METHOD OF TREATING INFLAMMATION

[75] Inventors: Alison M. Bendele, Greenfield; Henry U. Bryant, Indianapolis; John M. Schaus, Zionsville, all of Ind.

[73] Assignee: Eli Lilly and Company, Indianapolis, Ind.

[21] Appl. No.: 987,970

[22] Filed: Dec. 8, 1992

Related U.S. Application Data

[63] Continuation of Ser. No. 649,650, Jan. 31, 1991, abandoned.

[51] Int. Cl.⁶ ............................................. A61K 31/44
[52] U.S. Cl. .................... 514/288; 514/287; 514/292; 514/293
[58] Field of Search ................ 514/288, 292, 293, 287

[56] References Cited

U.S. PATENT DOCUMENTS

| | | | |
|---|---|---|---|
| 3,657,438 | 4/1972 | Blatter et al. | 424/248 |
| 3,752,814 | 8/1973 | Fluckiger et al. | 260/268 |
| 3,752,888 | 8/1973 | Fluckiger et al. | 260/268 |
| 3,790,577 | 2/1974 | Waring | 260/287 |
| 4,166,182 | 8/1979 | Kornfeld et al. | 546/67 |
| 4,198,415 | 4/1980 | Kornfeld et al. | 424/258 |
| 4,230,861 | 10/1980 | Kornfeld et al. | 424/258 |
| 4,235,909 | 11/1980 | Bach et al. | 424/258 |
| 4,468,401 | 8/1984 | Hahn | 542/82 |
| 4,501,890 | 2/1985 | Nichols et al. | 514/267 |
| 4,525,584 | 6/1985 | Gallick-Whitaker | 546/82 |
| 4,528,290 | 7/1985 | Wong et al. | 514/293 |
| 4,537,893 | 8/1985 | Titus et al. | 514/293 |
| 4,537,965 | 8/1985 | Gallick-Whitaker | 546/82 |
| 4,659,832 | 4/1987 | Schaus et al. | 546/83 |
| 4,675,322 | 6/1987 | Laguzza | 514/288 |
| 4,692,452 | 9/1987 | Cerny et al. | 514/288 |
| 4,826,986 | 5/1989 | Huser et al. | 546/153 |
| 4,980,358 | 12/1990 | Smith | 514/288 |

FOREIGN PATENT DOCUMENTS 138417  4/1985  European Pat. Off. ... C07D 471/04

OTHER PUBLICATIONS

Roitt, et al., *Immunology*, pp. 19, 10–11, 1985.
Oppenheim, et al., *Cellular Functions in Immunity and Inflammation*, pp. 10–11, 1981.
Bach, et al., *J. Med. Chem.*, 23, 481 (1980).
Nordman, et al., *J. Med. Chem.*, 28(3), 367 (1985).
Nagy E., et al., *Immunopharmacology*, 6, 231–243 (1983).
Berczi I., et al., *Arthritis and Rheumatism*, 27, 682–688 (1984).
Whyte A., and Williams R., *Arthritis and Rheumatism*, 31, 927–928 (1988).

*Primary Examiner*—Raymond Henley, III
*Attorney, Agent, or Firm*—John C. Demeter; John E. Parrish

[57] ABSTRACT

The present invention relates to the use of certain ergoline analogues and BCD tricyclic ergoline part-structure analogues as defined herein as anti-inflammatory agents.

7 Claims, 13 Drawing Sheets

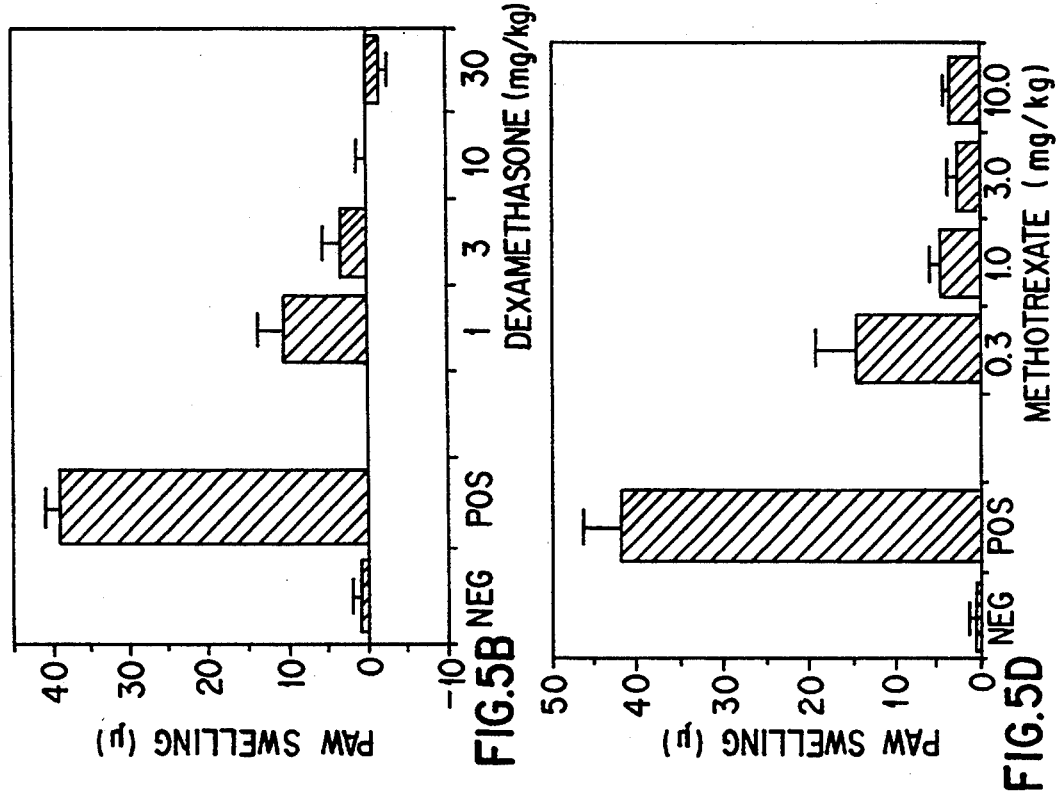
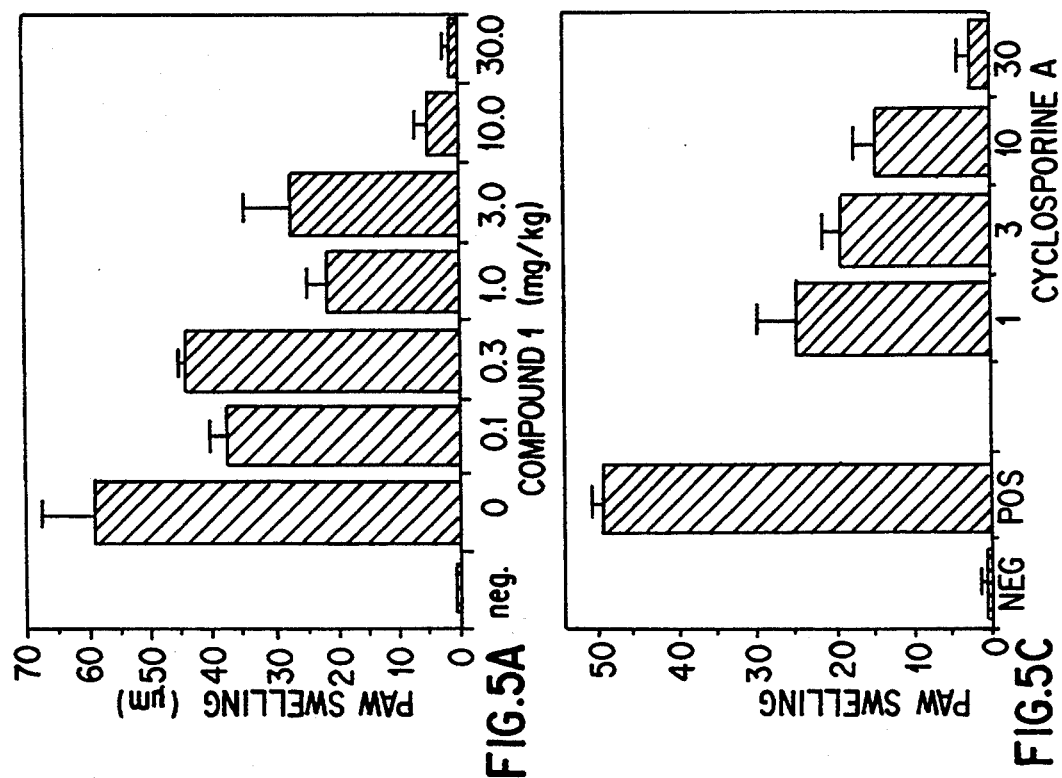

METHOD OF TREATING INFLAMMATION

This application is a continuation of application Ser. No. 07/649,650, filed Jan. 31, 1991, now abandoned.

The present invention relates to the use of certain ergoline analogues and BCD tricyclic ergoline part-structure analogues as anti-inflammatory agents.

BACKGROUND OF THE INVENTION

The ergoline ring is a tetracycle having the following structure

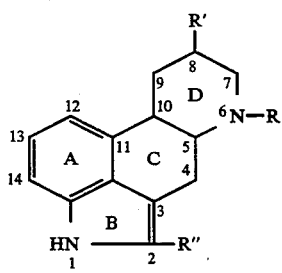

Certain substituted ergolines are known to be D-2 dopamine agonists having the ability to inhibit the secretion of prolactin and to affect favorably the symptoms of Parkinson's Syndrome. For example, in the foregoing structure when R is n-propyl, $R^1$ is methylthiomethyl, and R" is H, the substituted ergoline has been given the generic name pergolide, which is disclosed in U.S. Pat. No. 4,166,182. Pergolide has been proven to be effective in the treatment of some symptoms of Parkinsonism, and is being developed as the mesylate salt. Another such ergoline drug is α-bromo-ergocryptine, named generically as bromocryptine. It is disclosed in U.S. Pat. Nos. 3,752,814 and 3,752,888. For bromocryptine, R" is Br, R is methyl and R' is the ergocryptine side chain. While both ergolines are D-2 dopamine agonists, bromocryptine and pergolide also act at α adrenergic receptors.

BCD tricyclic ergoline part-structure compounds having the following formula

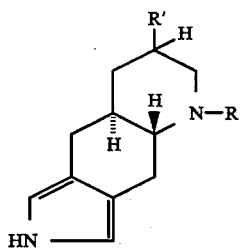

wherein R is lower alkyl, have been synthesized, and are disclosed in Bach et al., *J. Med. Chem.*, 23, 481 (1980) and U.S. Pat. No. 4,235,909. These products were prepared as racemates composed of the enantiomer illustrated above together with the mirror image thereof. In both enantiomers the R' substituent is equatorial. These compounds show activity in prolactin inhibition and rat-turning behavior tests, indicating that D-2 dopamine agonist activity is present. Related compounds in which the C-1 carbon is replaced by nitrogen to form a pyrazole ring are also disclosed by Bach et al. in *J. Med. Chem.*, 23, 481 (1980) and in U.S. Pat. No. 4,198,415. These pyrazoloquinolines are also D-2 dopamine agonists. They were prepared as the optically active isomers. See *J. Med. Chem.*, 26, 1112 (1983) and U.S. Pat. No. 4,567,266.

Other BCD tricyclic ergoline part-structure compounds having the following general formula

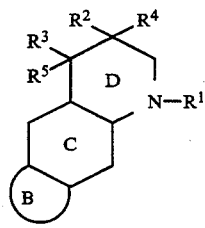

wherein the C- and D-rings are trans-fused and wherein the B-ring may be either a pyrimidine, thiazole, pyrazole, oxazole or pyrrole ring are disclosed in U.S. Pat. No. 4,826,986. These compounds are also D-2 dopamine agonists, and are prepared as racemates.

A number of diseases which have inflammatory components, beset mankind. Rheumatoid arthritis, contact hypersensitivities, and autoimmune syndromes are but a few examples of inflammatory processes which are driven by aberrant or uncontrolled activity of the immune system. Thus, it is not surprising that frequently, treatment of such inflammatory states has focused on disrupting the underlying immunological response, which in turn results in the abatement of the inflammatory manifestations of such disease states. Examples of clinical agents used in this approach include cyclosporine and methotrexate.

A significant limitation to the "treat the immunological aspect and the inflammation will subside" approach is the compromised immunological state of the host thus treated and the resultant vulnerability of the host to viral, bacterial and fungal infections as well as the potential for outgrowth of tumors which heretofore were held in check by an uncompromised immune system.

The alternate approach to clinical management of inflammatory diseases involves treatment with known anti-inflammatory agents such as steroids or preferably with non-steroidal anti-inflammatory drugs. Steroids are disfavored due to the numerous complications arising from therapy therewith. Likewise, the toxicities associated with many of the non-steroidal anti-inflammatory agents (NSAIDs) severely limits the clinical utility of NSAIDs.

The spectrum of inflammatory disease states, which lack a safe and effective therapy, presents a significant clinical problem. This problem is answered, in part, by the discovery that ergolines, possess anti-inflammatory activity. Surprisingly, the anti-inflammatory activity of the ergolines is not mediated by immunosuppressive effects. Thus, the now discovered direct anti-inflammatory activity of members of the ergolines allows clinical utilization of ergolines which heretofore would have been reserved due to the erroneous presumption that their anti-inflammatory activity was like bromocryptine merely a secondary effect of immunosuppressive activity.

It is one object of the present invention to provide methods of treating inflammation, and the accompanying pain and swelling in man and animals by administering certain ergoline or BCD tricyclic ergoline part-structure compounds.

Further objects will become apparent to those skilled in the art from the following description and claims.

SUMMARY OF THE INVENTION

In fulfillment of the above and other objects, this invention provides a method of treating inflammation in a mammal having inflammation comprising administering to said mammal an effective dose of a compound selected from: 8β-[(methoxy or methylthio) methyl]ergolines and 8β-[(methoxy or methylthio)methyl]8-ergolenes and their 2-aza analogues; and BCD tricyclic ergoline part-structures as further defined herein or a pharmaceutically acceptable acid addition salt of said compounds.

BRIEF DESCRIPTION OF THE FIGURES

FIG. 5 Dose response studies on the inhibitory effects of compound 1 (panel A) and a series of pharmacologic standards (dexamethasone, cyclosporine A and methotrexate, panels B through D, respectively) on the murine delayed type hypersensitivity response (DTH). NEG=negative control for DTH; POS=positive control for DTH.

DETAILED DESCRIPTION OF THE INVENTION

Figure 1A:
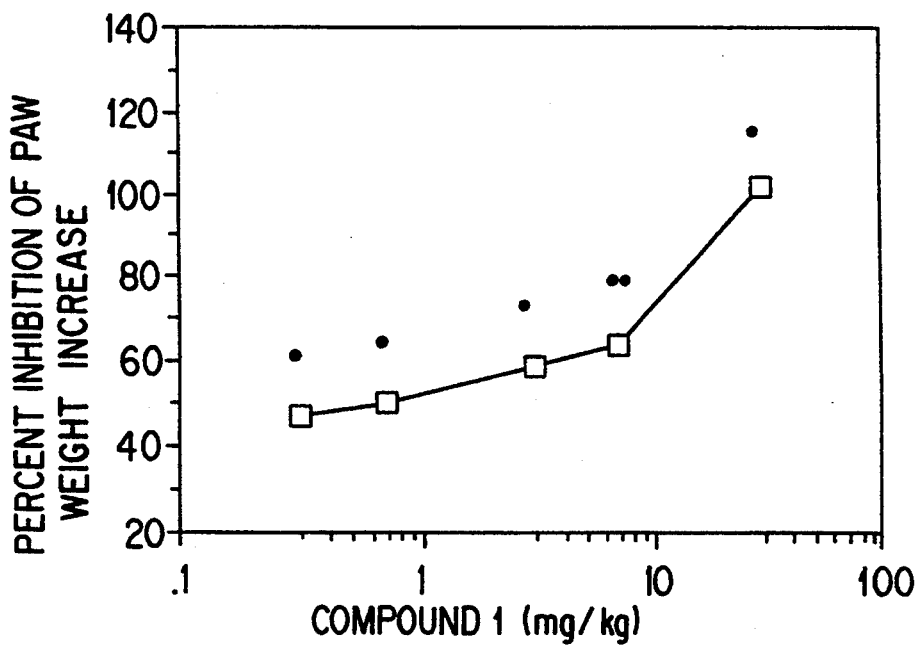
FIG. 1 Inhibitory effect of compound 1 on lipoidal amine arthritis induced increased in hind paw volume (panel A) and weight (panel B). *= $<0.05$ vs non-drug treated lipoidal amine injected controls.

The method of this invention is practiced by administering to a mammal having inflammation a compound selected from: 8β-[(methoxy or methylthio)methyl]ergolines and 8-[(methoxy or methylthio)methyl]8-ergolenes; and BCD tricyclic ergoline part-structures, or a pharmaceutically acceptable salt of said compounds. Preferably, the compound will be in the form of a pharmaceutically acceptable formulation.

Pharmaceutically acceptable acid addition salts of the compounds employed in the invention include salts derived from non-toxic inorganic acids such as: hydrochloric acid, nitric acid, phosphoric acid, sulfuric acid, hydrobromic acid, hydriodic acid, phosphorous acid and others, as well as salts derived from non-toxic organic acids such as aliphatic mono and dicarboxylic acids, phenyl-substituted alkanoic acids, hydroxyalkanoic and hydroxyalkandioic acid, aromatic acids, aliphatic and aromatic sulfonic acids. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenezenesulfonate, xylenesulfonate, phenylacetate, phenylpropionate, phenylbutyrate, citrate, lactate, β-hydroxybutyrate, glycollate, malate, naphthalene-1-sulfonate, naphthalene-2-sulfonate and mesylate. In addition, some of these salts may form solvates with water or organic solvents such as ethanol. These solvates are also included as compounds of this invention.

A first group of compounds employed in the method of the present invention comprises 8β-[(methoxy or methylthio)methyl]ergolines or 8β-[(methoxy or methylthio)methyl]-8-ergolenes and their 2 aza derivatives having the formula

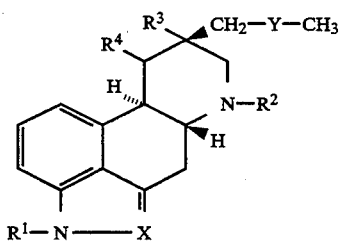

IA where
X is CH or N;
Y is O or S;
R¹ is 2-propenyl, $C_1$-$C_3$ alkyl, benzyl or substituted benzyl where the substitutents are one or two of the same or different and are selected from methyl, ethyl, methoxy, ethoxy, hydroxy, chloro, bromo, or fluoro;
R² is $C_2$-$C_3$ alkyl, allyl or cyclopropylmethyl;
R³ and R⁴ are both hydrogen or combine to form a carbon-carbon bond:
and pharmaceutically acceptable acid addition salts thereof.

A second group of compounds employed in the method of the present invention comprises BCD tricyclic ergoline part-structure compounds having the formula

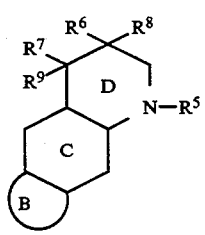

IB wherein:
R⁵ is $C_2$-$C_3$ alkyl, allyl or cyclopropylmethyl; the C and D rings are transfused;
R⁶ is hydrogen, $CH_2OH$, $CH_2OCH_3$, $CH_2SCH_3$, $CH_2SOCH_3$ or $CH_2SO_2CH_3$;
R⁷ is hydrogen or OH;
R⁸ and R⁹ are both hydrogen, or combine to form a carbon-carbon bond; provided that when R⁷ is OH, R⁸ and R⁹ are both hydrogen and

represents

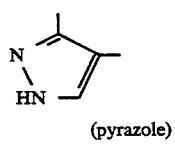

(a)

(pyrazole)

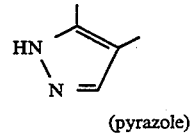

(b)

(pyrazole)

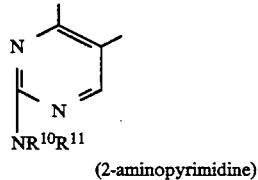

(c)

(2-aminopyrimidine)

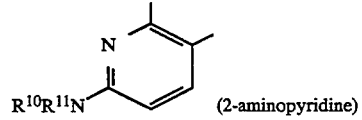

(d)

(2-aminopyridine)

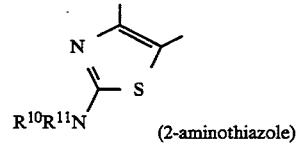

(e)

(2-aminothiazole)

where
R¹⁰ and R¹¹ are individually hydrogen, $C_1$-$C_3$ alkyl or benzyl;
and pharmaceutically acceptable acid addition salts thereof.

Preferred compounds of Formula IA are those where:
X is CH;
Y is S;
R¹ is hydrogen or isopropyl;
R² is n-propyl;
R³ and R⁴ are both hydrogen;
and pharmaceutically acceptable acid addition salts thereof.

Preferred compounds of Formula IB are those where:
R⁵ is n-propyl;
R⁶ is hydrogen, $CH_2OH$, $CH_2OCH_3$ or $CH_2SCH_3$;
R⁷ is hydrogen;
R⁸ and R⁹ are both hydrogen or combine to form a carbon-carbon bond; and

represents

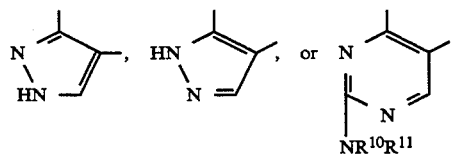

where $R^{10}$ and $R^{11}$ are both hydrogen, and pharmaceutically acceptable acid addition salts thereof.

Methods of preparing the compounds of Formula IA or their precursors are taught in U.S. Pat. Nos. 4,166,182 and 4,675,322, and in Bach et al., *J. Med. Chem.*, 23, 492–494 (1980) all of which are incorporated by reference herein in their entirety. Modifications to the above methods may be necessary to accommodate reactive functionalities of particular substituents. Such modifications would be both apparent, and known or readily ascertained, by those skilled in the art.

Methods of preparing the compounds of Formula IB or their precursors are taught in U.S. Pat. Nos. 4,826,986, 4,198,415, and 4,501,890 all of which are incorporated by reference herein in their entirety. Modifications to the above methods may be necessary to accommodate reactive functionalities of particular substituents. Such modifications would be both apparent, and known or readily ascertained by those skilled in the art.

Those compounds of Formula IB or their precursors which are pyrido[2,3-g] quinolines, are synthesized according to procedures taught in U.S. patent application Ser. No. 514,631, filed Apr. 25, 1990, entitled "Pryidoquinoline Dopamine Agonists, Compositions and Use", which is incorporated by reference herein in its entirety. These procedures are shown in the following scheme. Although only one of the optical enantiomers is illustrated, one skilled in the art will readily appreciate the synthetic scheme illustrated is applicable to preparing the opposite optical enantiomer as well as to the racemic mixture itself.

Scheme I

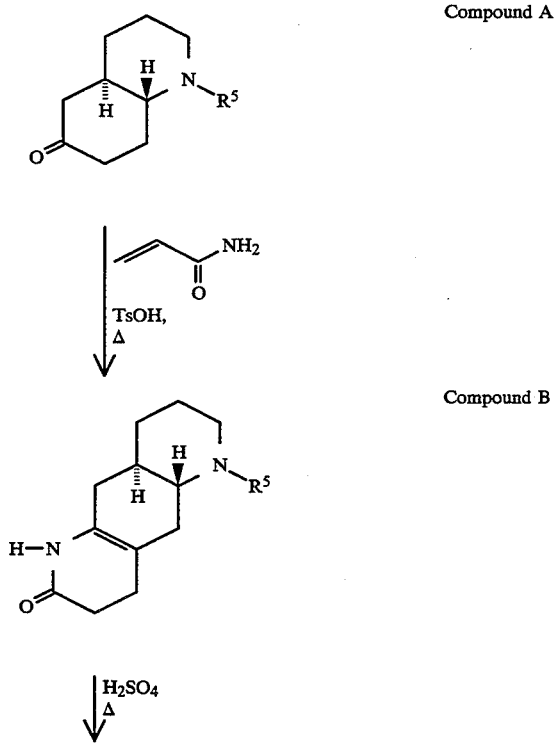
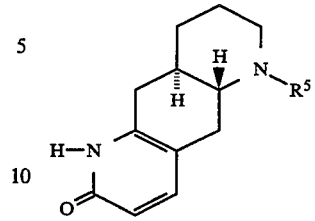
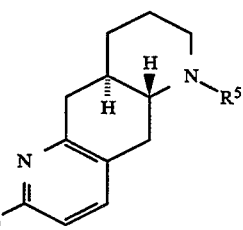

Compound A

Compound B

Compound C

Compound D

Compounds represented by Compound D in Scheme I are most easily prepared by utilizing a ketone starting material (Compound A) wherein $R^5$—is $C_2$-$C_3$ alkyl, allyl or cyclopropylmethyl. The ketones represented by Compound A are preferably prepared as taught by Schaus, U.S. Pat. No. 4,540,787, issued Sep. 10, 1985, incorporated herein by reference. The ketone (either resolved or racemic) can then be reacted with acrylamide, p-toluenesulfonic acid monohydrate, and p-methoxyphenol in an inert solvent, with heat, to form Compound B, wherein $R^5$ is as set forth above.

Compound B is next dehydrogenated using concentrated sulfuric acid and heat. The resultant Compound C, a trans-2-oxo-6-(substituted)-1,2,5,5a,6,7, 8,9,10-decahydropyrido[2,3-g]quinoline, is used as the basic intermediate for the synthesis of Compound D variants.

Compounds represented by Compound D are prepared by reacting Compounds C with a dehydrating halogenating agent such as phosphorous oxychloride, phosphorous pentachloride, phosphorous tribromide, phosphorous triiodide, sulfur tetrafluoride, diethylaminosulfur trifluoride, or the like, to yield Compound D. Said halogenated compounds serve as intermediates in the synthesis of the pyrido [2,3-g]quinolines of Formula IB.

Displacement of the halogen atom by an amine provides the pyrido[2,3-g]quinolines of Formula IB.

Thus, in general, nucleophilic displacement of the 2-halo substituent may be effected through the use of a variety of mono-substituted and di-substituted amine salts to provide the pyrido[2,3-g]quinoline compounds of Formulae IB. The only functional limitation is that said amine salts must have melting points in the range of from about 170° C. to about 250° C.

The compounds employed as initial starting materials in the synthesis of the compounds used in the method of the present invention are well known and, to the extent not commercially available, are readily synthesized by standard procedures commonly employed by those of ordinary skill in the art.

As mentioned hereinabove, the invention includes pharmaceutically acceptable acid addition salts of the compounds defined by the above formulae. Since these compounds are amines, they are basic in nature and accordingly react with any of a number of inorganic and organic acids to form pharmaceutically acceptable acid addition salts. Since the free amines of the compounds of this invention are typically oils at room temperature, it is preferable to convert the free amines to their corresponding pharmaceutically acceptable acid addition salts for ease of handling and administration, since the later are routinely solid at room temperature.

In addition, some of these salts may form hydrates or solvates with water or organic solvents. Such hydrates and solvates also are included as compounds useful in the method of the present invention.

The pharmaceutically acceptable acid addition salts of the invention are typically formed by reacting a compound of Formula IA or IB with an equimolar or excess amount of acid. The reactants are generally combined in a mutual solvent such as diethyl ether or benzene, and the salt normally precipitates out of solution within about one hour to 10 days, and can be isolated by filtration or the solvent is stripped off by conventional means.

The present invention provides a method of treating inflammation in mammals comprising administering to a mammal having inflammation an effective amount of a compound having Formula IA or IB, or a pharmaceutically acceptable acid addition salt thereof.

The term "effective amount" as used herein, means an amount of a compound of the present invention which is capable of reducing inflammation and is not toxic to the recipient thereof. The specific dose of compound administered according to this invention will, of course, be determined by the particular circumstances surrounding the case, including, for example, the compound administered, the route of administration, and the condition being treated. A typical daily dose will contain from about 0.01 mg/kg to about 20 mg/kg and ideally from about 0.1 to about 5 mg/kg.

The compounds can be administered by a variety of routes including oral, rectal, transdermal, subcutaneous, intravenous, intramuscular, and intranasal.

Preferably, the compounds are formulated prior to administration. These pharmaceutical formulations comprise an effective amount of a compound of Formula IA or IB or a pharmaceutically acceptable salt thereof in association with a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recepient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gumacacia, calcium phosphate, alginates, tragacanth, gelatin, calcium silicate, microcrystalline cellulose, polyvinylpyrrolidone, cullulose, water syrup, methyl cellulose, methylhydroxybenzoates, propylhydroxybenzoates, propylhydroxybenzoates, talc, magnesium stearate and mineral oil. The formulations may additionally include lubricating agents, wetting agents, emulsifying agents, suspending agents, preserving agents, sweetening agents, flavoring agents, and the like. The compositions may be formulated so as to provide quick, sustained or delayed release of the active ingredient after administration to the patient by employing procedures well known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The anti-inflammatory activity of the compounds employed in the method of the present invention was established by the following procedures.

Figure 1B:
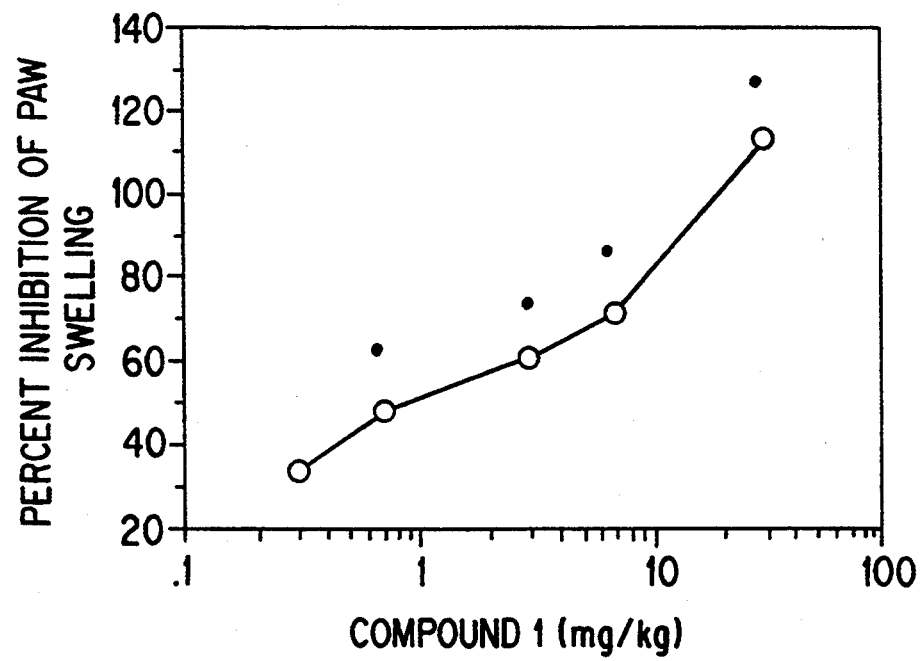

The anti-inflammatory activity in the absence of observable immunosuppression of the compounds of the present invention was established in a variety of animal models including lipoidal amine induced arthritis and acute paw inflammation models. Lipoidal amine induced polyarthritis is an animal arthritis model originally described by Chang, Y., et al. in *Arthritis and Rheumatism* 23:62–71 (1980). The lipoidal amine induced polyarthritis results from injection of N,N-dioctadecyl-$N^1$,N-bis(2-hydroxyethyl) propanediamine (7.5 mg/kg Lewis rat (220–225 g)), which is suspended in oil, intradermally at the base of the tail. FIG. 1 provides dose response curves obtained through treatment of rats with compound D-1-isopropyl-6-n-propyl-8β-methylthiomethyl ergoline as the hydrochloride salt. A statistically significant decrease in both paw volume (Panel A) and paw weight (Panel B) was observed at D-1-isopropyl-6-n-propyl-8β-methylthiomethyl ergoline dosages of 0.7 mg/kg and greater. Administration of pergolide to rats in the lipoidal amine arthritis assay resulted in statistically significant suppression of paw volume and paw weight at doses of 3 mg/kg and greater.

Acute inflammation models were performed to demonstrate the anti-inflammatory activity of the ergoline compounds of the invention as follows. In one such model, the acute paw inflammation model, rats were treated with test compounds one hour prior to plantar injection of a 50 μl volume of a phlogistic. Animals were sacrificed and paw weights were determined at a prescribed time interval following the plantar injections. When 1% carrageenan was used as the phlogistic, the time interval between injection and sacrifice was 3 hours. When serotonin (5-hydroxytryptamine (5-HT)) was used, as the phlogistic agent the time interval was one hour. When substance P was used, the time interval was 30 minutes. The acute paw inflammation model is described in more detail in Example 3.

The anti-inflammatory activity of pergolide, bromocryptine, and fenoprofen was compared in the acute inflammatory response model disclosed in Example 3. The results of these studies are summarized in Table 1 and Table 2 below.

TABLE 1

ANTI-INFLAMMATORY EFFECTS IN RATS TREATED WITH SINGLE ORAL DOSES OF PERGOLIDE OR FENOPROFEN IN THE CARRAGEENAN EDEMA MODEL.

| Group | Dose (mg/kg) | Paw Weight Difference (g) | % Inhibition |
| --- | --- | --- | --- |
| Control | 0.0 | 0.730 ± 0.054 | 0 |
| Pergolide | 0.3 | 0.290 ± 0.028* | 60 |
| Pergolide | 1.0 | 0.295 ± 0.019* | 60 |
| Pergolide | 3.0 | 0.292 ± 0.017* | 60 |
| Pergolide | 10.0 | 0.293 ± 0.018* | 60 |
| Fenoprofen | 30.0 | 0.353 ± 0.043* | 52 |

*$p \leq 0.05$, Two tailed Dunnett T on Raw Data.

TABLE 2

ANTI-INFLAMMATORY EFFECTS IN RATS TREATED WITH SINGLE ORAL DOSES OF PERGOLIDE, BROMOCRIPTINE, OR FENOPROFEN IN THE CARRAGEENAN EDEMA MODEL.

| Group | Dose (mg/kg) | Paw Weight Difference (g) | % Inhibition |
| --- | --- | --- | --- |
| Control | 0.0 | 0.846 ± 0.048 | 0 |
| Pergolide | 0.01 | 0.820 ± 0.033 | 1 |
| Pergolide | 0.03 | 1.009 ± 0.056 | 0 |
| Pergolide | 0.1 | 0.751 ± 0.045 | 11 |
| Pergolide | 0.3 | 0.313 ± 0.045* | 63 |
| Bromocriptine | 0.1 | 0.923 ± 0.039 | 0 |
| Bromocriptine | 0.3 | 0.937 ± 0.060 | 0 |
| Bromocriptine | 1.0 | 0.803 ± 0.046 | 0 |
| Bromocriptine | 3.0 | 0.931 ± 0.067 | 0 |
| Fenoprofen | 30.0 | 0.379 ± 0.028* | 55 |

*$p \leq 0.05$, Two tailed Dunnett T on Raw Data.

The significant anti-inflammatory properties of pergolide are evident in the data above. Interestingly, bromocriptine displayed no activity in the acute inflammation model at doses as high as 3 mg/kg, po. Thus, bromocriptine's activity in inflammatory models as described in the literature [Nagy, E., Berczi, I., Wien, G. E., Asa, S. L. amd Kovacs, K., Immunomodulation by bromocriptine, *Immunopharmocology* 6:231-243 (1983); Berczi, I., Nagy, E., Asa, S. L. and Kovacs, K., The influence of pituitary hormones on adjuvant arthritis, *Arthritis and Rheumatism* 27:682-688 (1984); Whyte, A., and Williams, R. O., Bromocryptine suppresses post-partum exacerbation of collagen-induced arthritis, *Arthritis and Rheumatism* 31:927-928 (1988)] is due to immunosuppressive activity. Fenoprofen which was included as a control compound, was not as effective as pergolide in suppressing inflammation even when tested at 30 mg/kg. In separate studies, the isopropyl derivative of pergolide, D-1-isopropyl-6-n-propyl-8β-methylthiomethyl ergoline also inhibited carrageenan induced paw swelling with an ED$_{50}$ value of approximately 0.3 mg/kg.

Figure 2A:
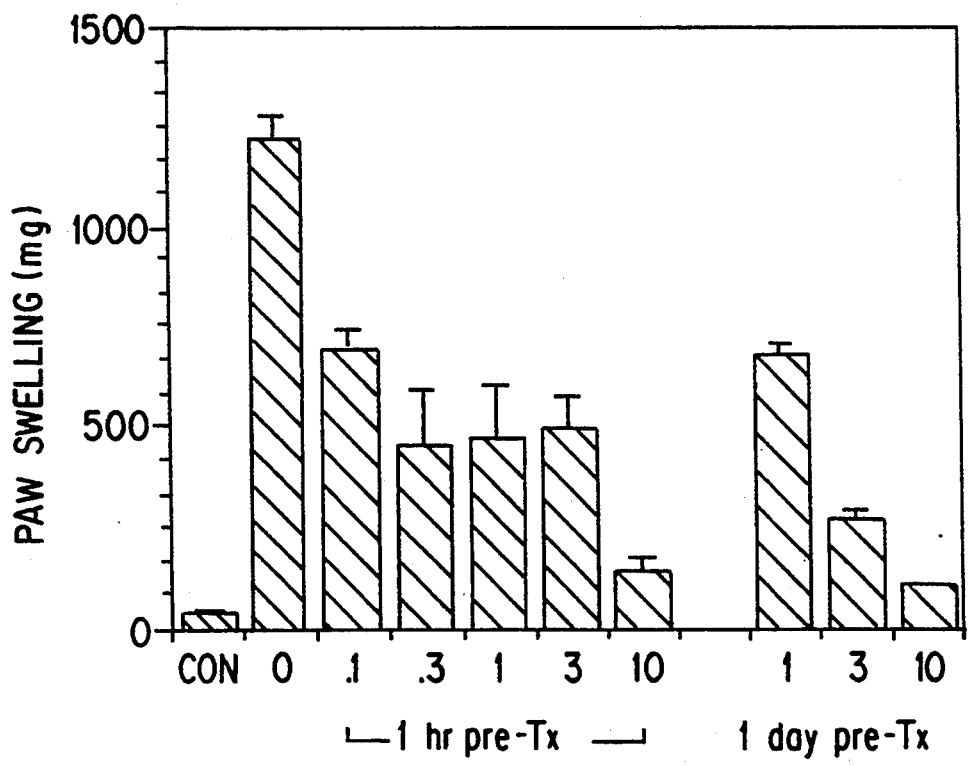
FIG. 2 Inhibitory effect of compound 1 on sertonin (0.2 mg/ml serotonin) induced paw swelling (panel A) and the effect of compound 2 on serotonin (0.005 to 0.2 mg/kg) induced paw swelling (panel B). The duration of action following single injection of compound 1 may be observed at 1 hour or 24 hours following a single injection (Panel A).
Figure 2B:
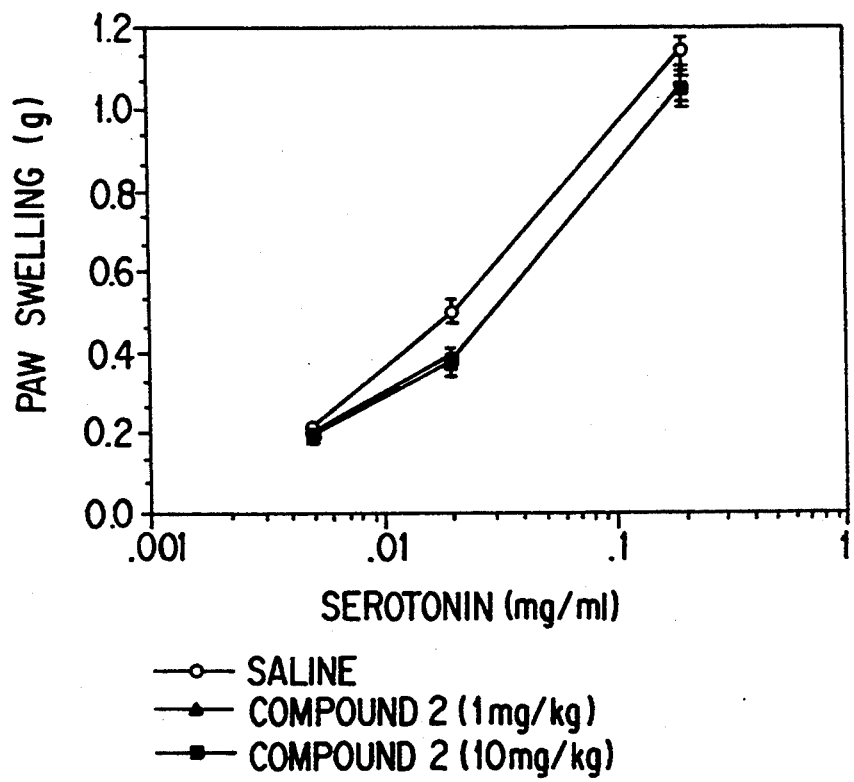
Figure 3:
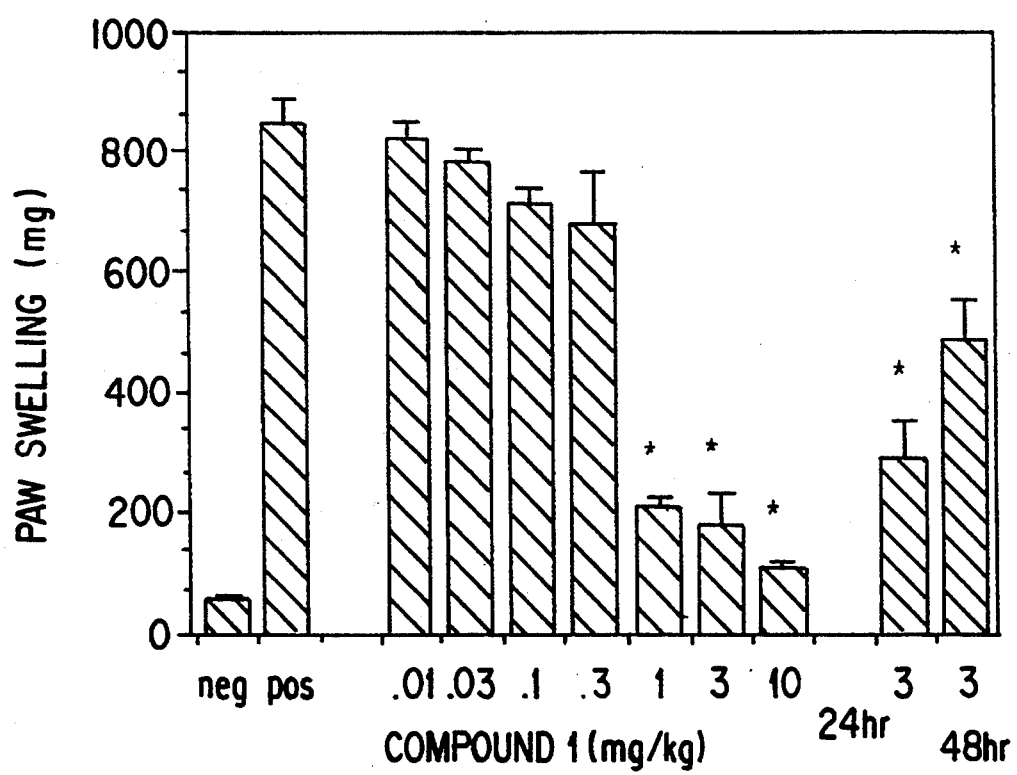
FIG. 3 Inhibition of serotonin (0.2 mg/kg) induced paw swelling by compound 1, at 1 hour, 24 hour and 48 hour following a single injection. *= $<0.05$ vs positive control (pos). neg=negative control.

The effect of D-1-isopropyl-6-n-propyl-8β-methylthiomethyl ergoline in 5-HT induced acute paw inflammation is presented in FIG. 2. As FIG. 2, Panel A indicates D-1-isopropyl-6-n-propyl-8β-methylthiomethyl ergoline dosages of as little as 100 μg/kg resulted in a significant reduction in paw swelling. FIG. 2, Panel B illustrates the ability of pergolide to diminish 5-HT induced paw swelling. Furthermore, the anti-inflammatory effect of D-1-isopropyl-6-n-propyl-8β-methylthiomethyl ergoline is longlasting. FIG. 3 provides data illustrating the duration of D-1-isopropyl-6-n-propyl-8β-methylthiomethyl ergoline activity in the 5-HT paw swelling assay. The significant reduction in paw swelling obtained when animals were dosed with 3 mg/kg of D-1-isopropyl-6-n-propyl-8β-methylthiomethyl ergoline at 24 and 48 hours prior to phlogistic challenge document the long-lasting anti-inflammatory activity of D-1-isopropyl-6-n-propyl-8β-methylthiomethyl ergoline.

The isopropyl derivative of pergolide also suppressed the acute inflammatory response to substance P. Substance P (0.01 mg/ml, interplanter) induced a 174 ±18 mg increase in paw weight in normal rats, but only a 38±11 mg increase in rats pre-treated with 3 mg/kg D-1-isopropyl-6-n-propyl-8β-methylthiomethyl ergoline (49% reduction, $p<0.05$).

The acute inflammation assay of Example 3 provides a useful method for identifying anti-inflammatory agents. Animals preferred for use in the acute inflammation assay include rats, mice, guinea pigs and rabbits while mice and rats are more preferred with mice being especially preferred. Phlogistic agents preferred for use in the acute inflammation assay include carrageenan, 5-HT and substance P. The preferred time point at which inflammation is measured depends upon the phlogistic agent used and the rate at which inflammation results therefrom. The optimal time point of measurement can be determined through routine experimentation. The present inventors have determined that one hour following injection of 5-HT, or 180 minutes following injection of carrageenan, or 30 minutes following injection with substance P are preferred time points, but as stated above other time points are also well suited and thus a range of time points are contemplated by the present invention.

Figure 4A:
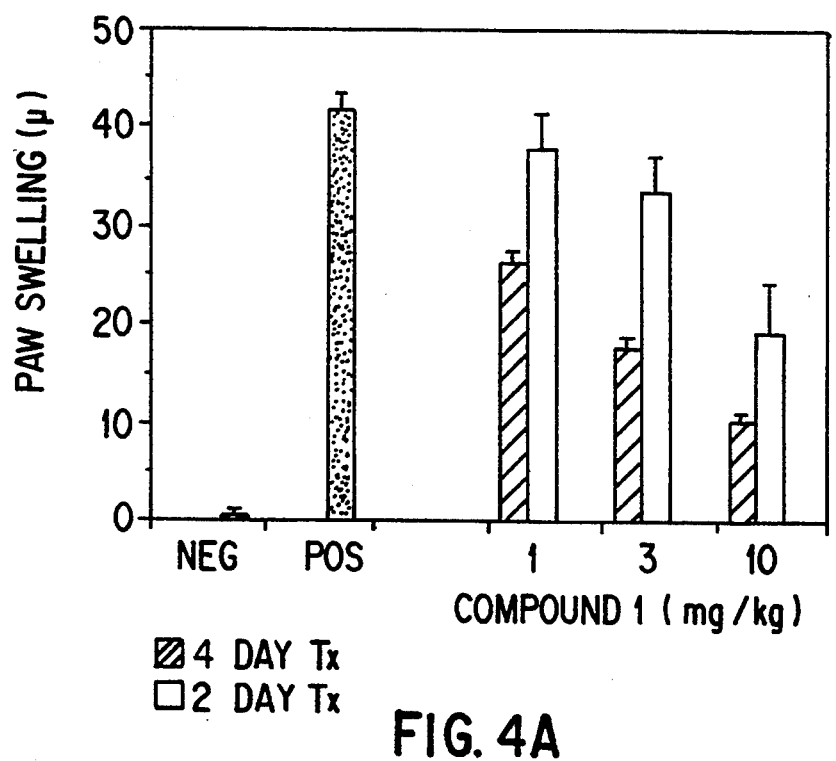
FIG. 4 Effect of 2 or 4 days treatment with compound 1 on a murine delayed type hypersensitivity (DTH) response (panel A) and toxicity study with compound 1 in mice (panel B). NEG=negative control for DTH; POS=positive control for DTH; CMC=carboxymethylcellulose (vehicle).
Figure 4B:
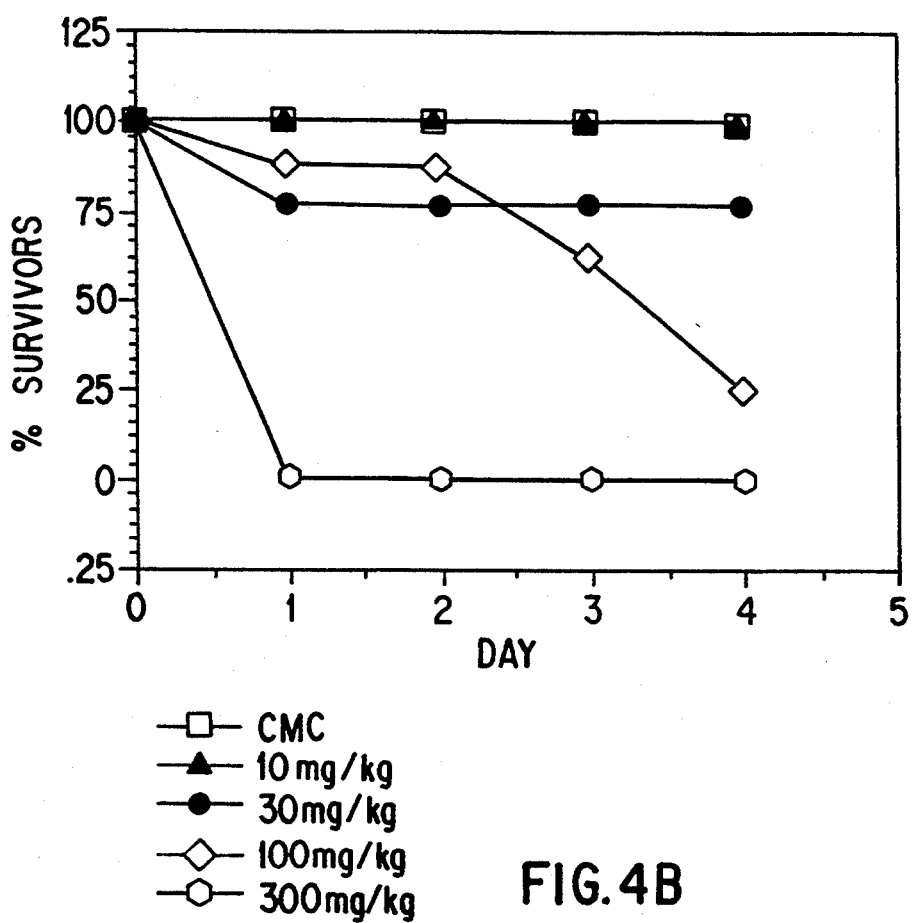

The activity of ergoline compounds was also evaluated in a murine delayed-type hypersensitivity (DTH) assay. The DTH assay was performed in substantial accordance with the method set forth in Example 1. Briefly, mice were sensitized by topical administration of picryl chloride on day 1 of the assay. On day 4 paw size was determined and recorded and the paw was then challenged with picryl chloride. The challenged paw was remeasured on day 5 to quantitate the DTH response via the increase in paw size. Results of the effects of compound D-1-isopropyl-6-n-propyl-8β-methylthiomethyl ergoline in the murine DTH model are presented in FIG. 4. FIG. 4, Panel A illustrates the efficacy of compound D-1-isopropyl-6-n-propyl-8β-methylthiomethyl ergoline in reducing paw swelling. Treatment of animals for 4 days resulted in a superior efficacy as compared to the two day treatment schedule. FIG. 4, Panel B is a survival curve of mice treated with varying dosages of D-1-isopropyl-6-n-propyl-8β-methylthiomethyl ergoline. The results of FIG. 3 clearly indicate that compound D-1-isopropyl-6-n-propyl-8β-methylthiomethyl ergoline shows efficacy in the murine DTH model at dosages well within the toxic level of the comcpound.

Compounds of the present invention were evaluated for their anti-inflammatory activity in the DTH assay. These compounds are set forth below in Table A.

TABLE A

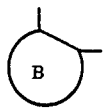

| Compound Example No. | Structure | X | Y | R¹ | R² | R³ | R⁴ | R⁵ | R⁶ | R⁷ | R⁸ | R⁹ | B |
|---|---|---|---|---|---|---|---|---|---|---|---|---|---|
| 1 | IA | CH | S | i-Pr | n-Pr | H | H | — | — | — | — | — | |
| 2 (pergolide) | IA | CH | S | H | n-Pr | H | H | — | — | — | — | — | |
| 3 | IA | CH | O | i-Pr | n-Pr | H | H | — | — | — | — | — | |
| 4 | IA | N | S | H | n-Pr | H | H | — | — | — | — | — | |
| 5 | IB | — | — | — | — | — | — | n-Pr | H | H | H | H | pyrazole |
| 6 | IB | — | — | — | — | — | — | n-Pr | H | H | H | H | 2-amino thiazole |
| 7 | IB | — | — | — | — | — | — | n-Pr | H | H | H | H | 2-amino pyrido |
| 8 | IB | — | — | — | — | — | — | n-Pr | H | OH | H | H | 2-amino pyrimidine |
| 9 | IB | — | — | — | — | — | — | n-Pr | CH₂OH | H | -bond- | | pyrazole |
| 10 | IB | — | — | — | — | — | — | n-Pr | CH₂OH | H | H | H | pyrazole |

Figure 6A:
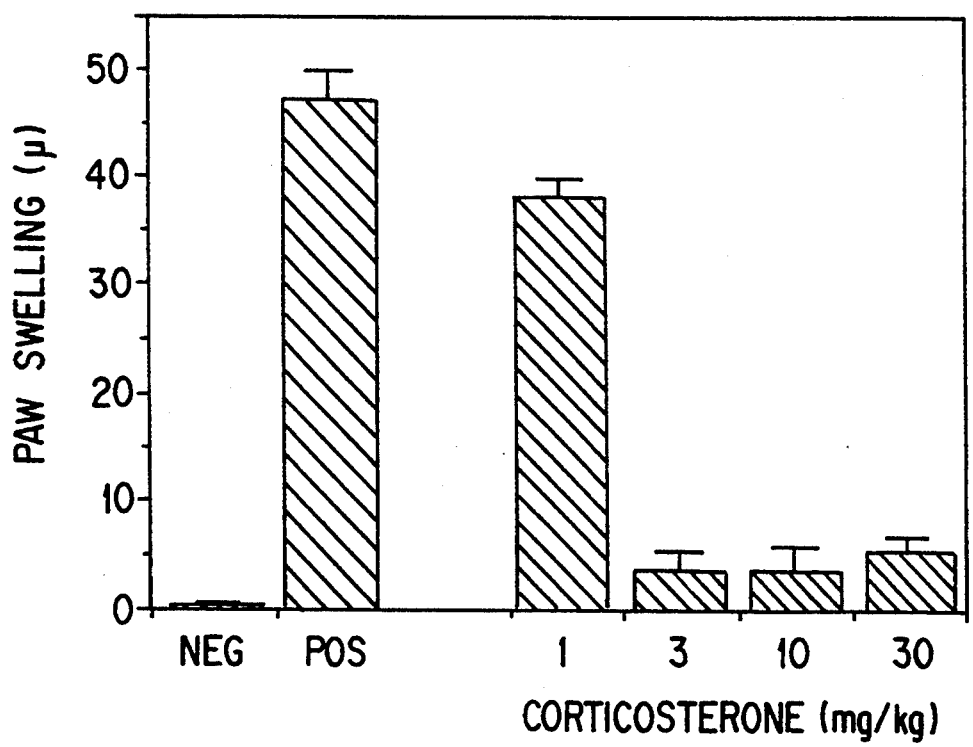
FIG. 6 Dose response studies on the inhibitory effects of additional pharmacologic standards (corticosterone—panel A; and azathioprine—panel B) on the murine delayed type hypersensitivity (DTH) response. NEG=negative control for DTH; POS=positive control for DTH.
Figure 6B:
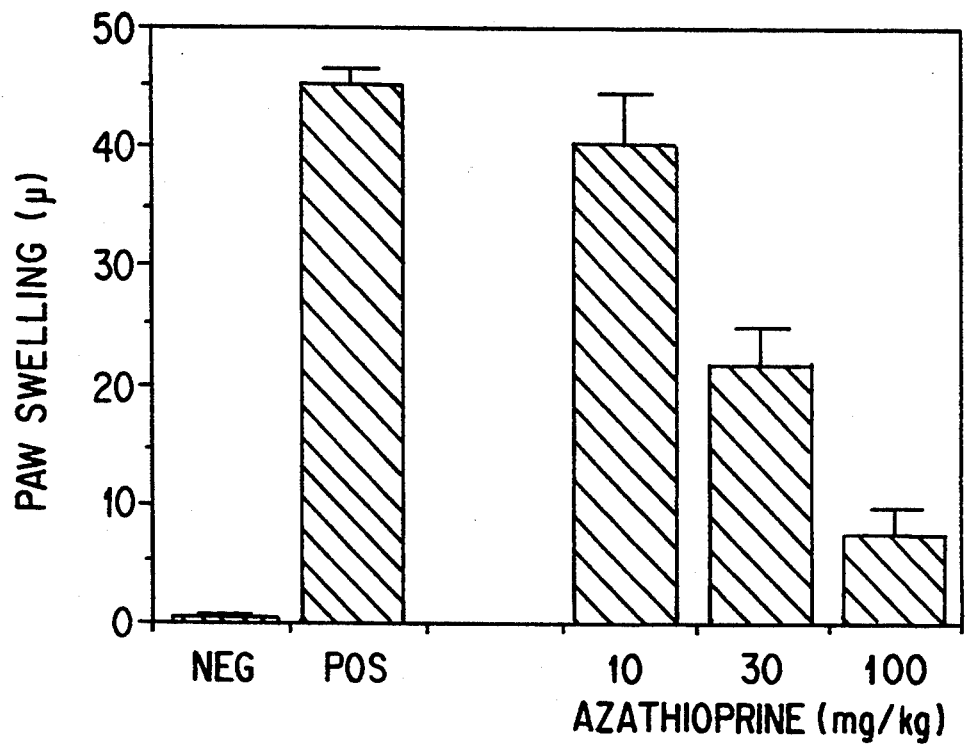

The activity of D-1-isopropyl-6-n-propyl-8β-methylthiomethyl ergoline in the DTH assay was compared to a variety of known anti-inflammatory compounds to provide a pharmacologic profile of D-1-isopropyl-6-n-propyl-8β-methylthiomethyl ergoline. FIGS. 5 and 6 provide comparative dose response curves for D-1-isopropyl-6-n-propyl-8β-methylthiomethyl ergoline FIG. 5, (Panel A), dexamethasone FIG. 5, (Panel B), cyclosporine, FIG. 5 (Panel C), methotrexate FIG. 5, (Panel D), cortisosterone FIG. 6 (Panel A), and azathioprine FIG. 6 (Panel B).

Figure 7A:
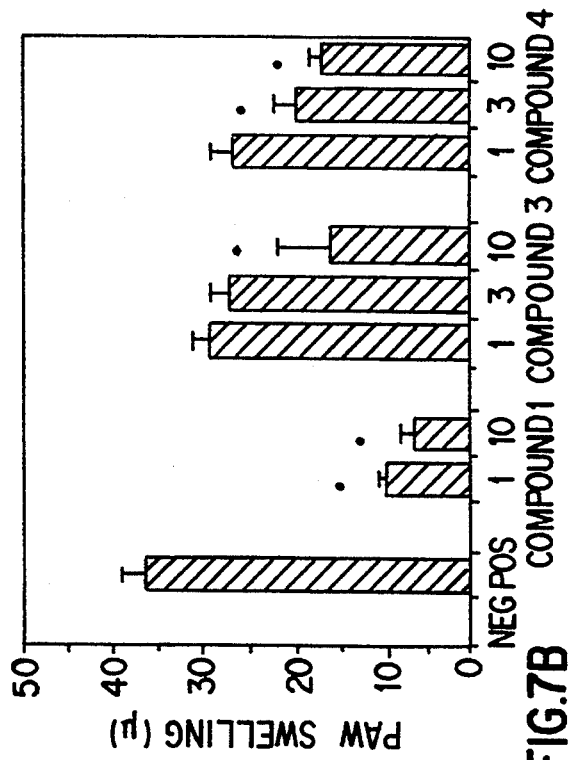
FIG. 7 Dose response studies on the inhibitory effects of various ergoline compounds (compounds 1 and 2—panel A; compounds 1, 3 and 4—panel B; and compounds 1 and 5—panel C) on the murine delayed type hypersensitivity (DTH) response. NEG=negative control for DTH; POS=positive control for DTH. *=$p<0.05$ vs POS.
Figure 7B:
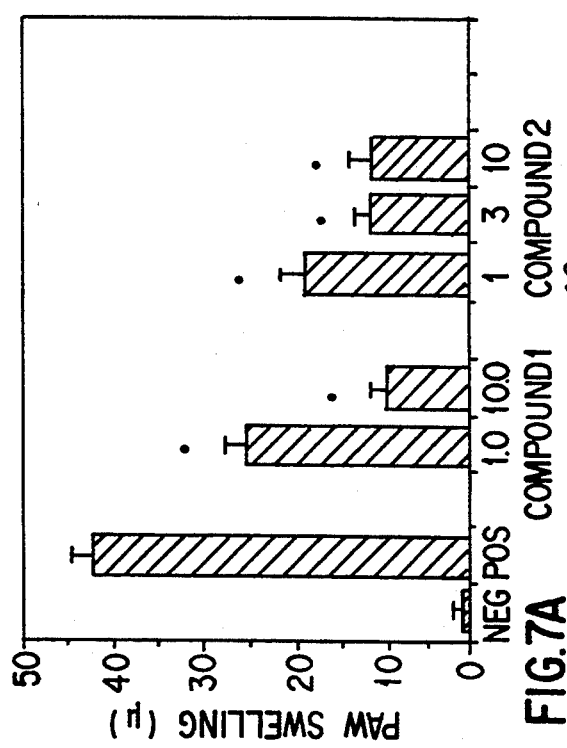
Figure 7C:
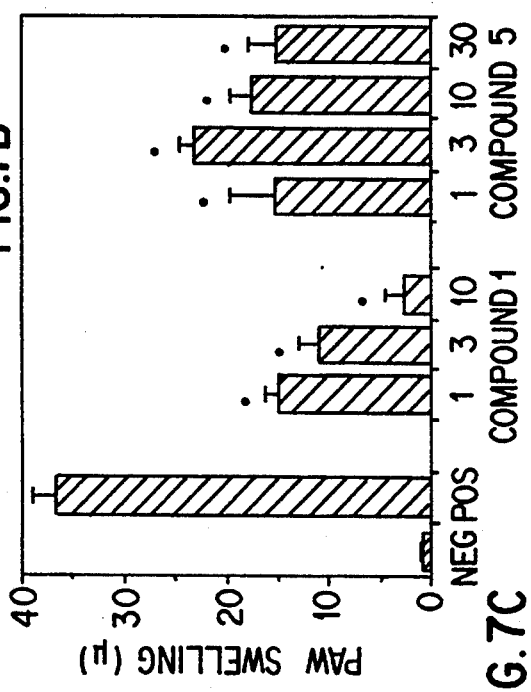
Figure 8A:
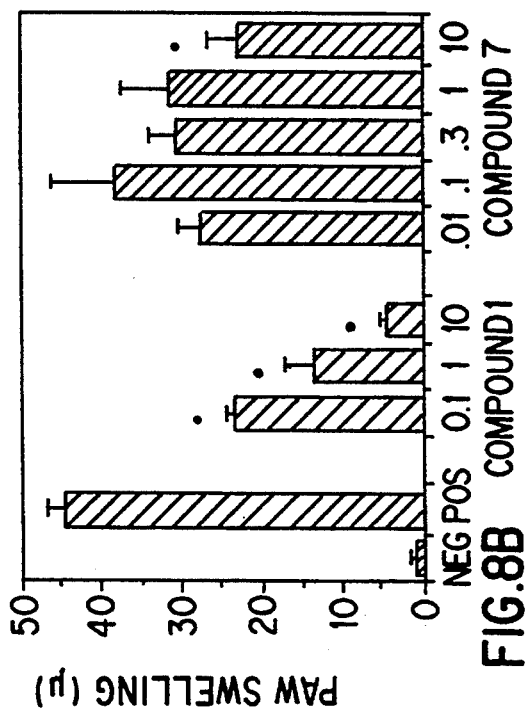
FIG. 8 Dose response studies on the inhibitory effects of various ergoline compounds (compounds 1 and 6—panel A; compounds 1 and 7—panel B; lack of inhibition with compound 8—panel C; and inhibition with compound 9—panel D) on the murine delayed type hypersensitivity (DTH) response. NEG=negative control for DTH; POS—positive control for DTH. *=$p<0.05$ vs POS.
Figure 8B:
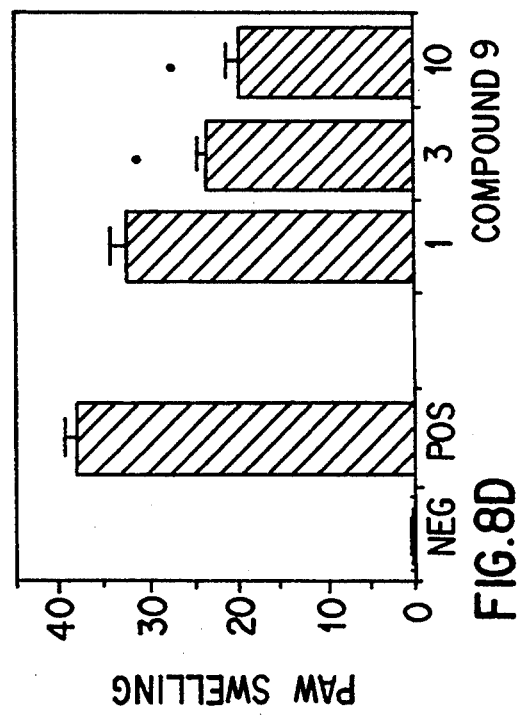
Figure 8C:
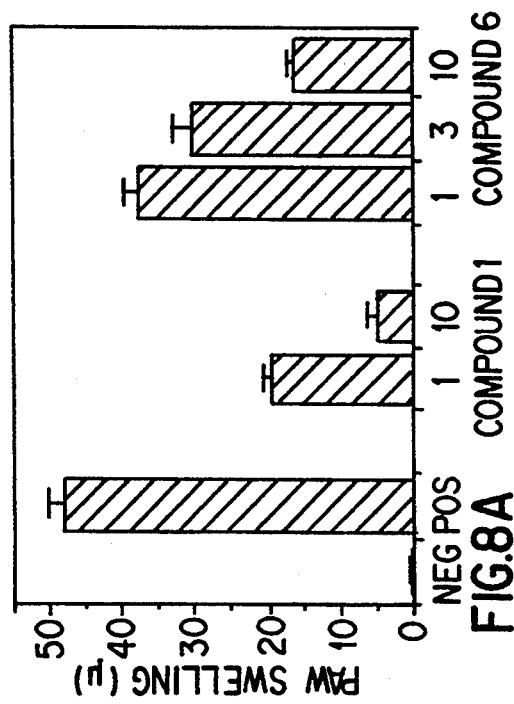
Figure 8D:
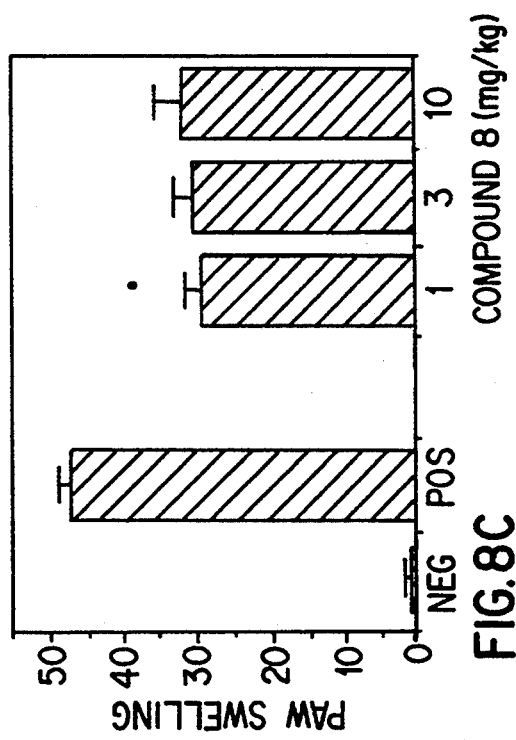

Compound D-1-isopropyl-6-n-propyl-8β-methylthiomethyl ergoline is a preferred ergoline for purposes of the present invention. However, other ergolines also have anti-inflammatory activity. Surprisingly, a related ergoline, D-6-n-pentyl-8β-methylthiomethyl ergoline, showed no anti-inflammatory activity. This particular structure also shows minimal affinity at the dopamine receptor indicating the importance of interaction with this receptor type for the anti-inflammatory activity. Results of these studies are illustrated in FIGS. 7–9A. Pergolide (FIG. 7, Panel A) significantly reduced paw swelling at dosages of 1, 3 and 10 mg/kg. Compound D-6-n-propyl-8β-methylthiomethyl ergoline, (FIG. 7, Panel B) demonstrated anti-inflammatory activity at dosages of 1, 3 and 10 mg/kg, yet only the 10 mg/kg dosage yielded a statistically significant reduction in paw swelling. Compound D-2-aza-6-n-propyl-8β-methylthiomethyl ergoline (FIG. 7, Panel B) reduced paw swelling at dosages of 1, 3 and 10 mg/kg with the 3 mg/kg and 10 mg/kg reductions being statistically significant. Compound trans-(±)-5-n-propyl-4,4a,5,6,7,8,8a,9-octahydro-1H-pyrazolo[3,4-g] quinoline significantly reduced paw swelling at dosages of 1, 3 10 and 30 mg/kg (FIG. 7, Panel C). The reductions in paw swelling when compounds trans-(±)-2-amino-5-n-propyl-4,4a,5,6,7,8,8a,9-octahydrothiazolo [4,5-g] quinoline (FIG. 8, Panel A) and trans-(±)-2-amino-6-propyl-5,5a,6,7,8,9,9a,10-octahydropyrido [2-3 g] quinoline (FIG. 8, Panel B) were dosed at 10 mg/kg was statistically significant. Compound trans-(±)-2-amino-6-n-propyl-5,5a,6,7,8,9,9a,10-octahydropyrimido[4,5-g] quinoline) (FIG. 8, Panel C) demonstrated a statistically significant decrease in inflammation at 1 mg/kg, while the decrease in inflammation associated with administration of 7-(5-n-propyl-trans-4,4a,5,6,8a,9-hexahydro-2H-pyrazolo[3,4-g) quinoline) methanol (FIG. 8, Panel D) and 7-(5-n-propyl-trans-4,4a,5,6,7,8,8a, 9-Octahydro-2H-pyrazolo[3,4-g] quinoline) methanol (FIG. 9, Panel A) was statistically significant at the 3 mg/kg and 10 mg/kg dosage levels.

Figure 9A:
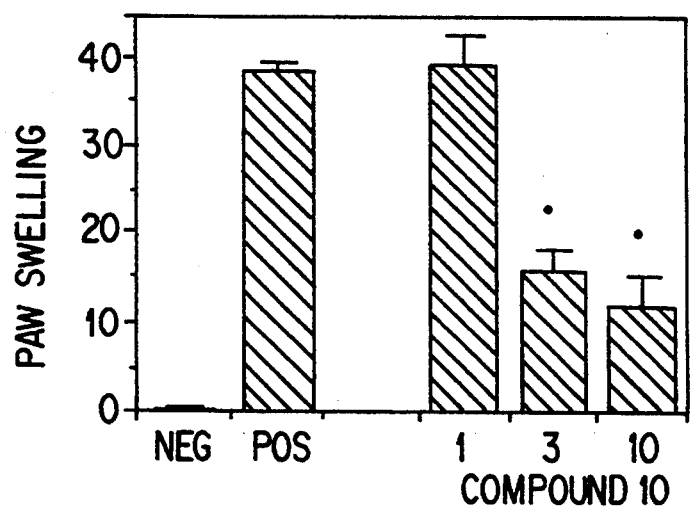
FIG. 9 Dose response studies on the inhibitory effects of compound 10 in the murine delayed type hypersensitivity (DTH) response (panel A) and the reversal of inhibition of the DTH by compound 1 when animals are pretreated with the dopamine receptor antagonists, domperidone (panel B) and sulpiride (panel C). NEG=negative control for DTH; POS=postivity control for DTH. *=$p<0.05$ vs POS in panel A and vs 0 domperidone group in panel B. a=$p<0.05$ vs POS and b=$p<0.05$ vs 0 sulpiride group in panel C.
Figure 9B:
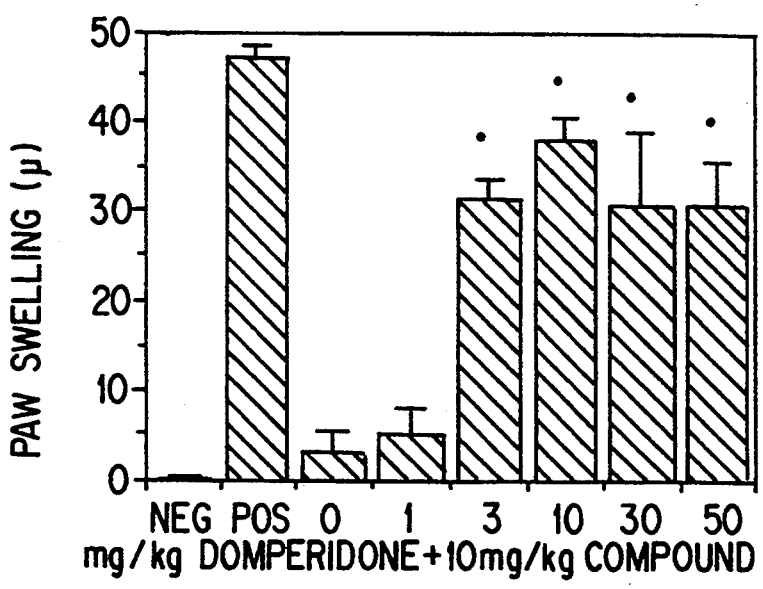
Figure 9C:
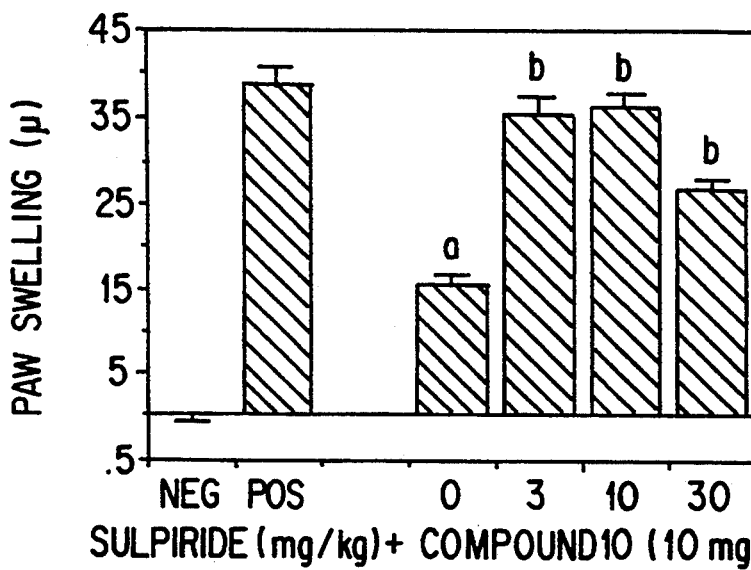

The anti-inflammatory activity of the ergoline compounds of the invention may also be due at least in part to dopamine agonist activity of the compounds. Support for this presumed mechanism of action is found in the data of FIG. 9, Panel B. FIG. 9, Panel B illustrates the effect of administering domperidone, a well-known peripherally restricted dopamine antagonist, in conjunction with the illustrative ergoline D-1-isopropyl-6-n-propyl-8β-methylthiomethyl ergoline. Domperidone reversed the anti-inflammatory activity of D-1-isopropyl-6-n-propyl-8β-methylthiomethyl ergoline as indicated in FIG. 9, Panel B. A similar effect was seen when the dopamine antagonist sulpiride was administered to 7-(5-n-propyl-trans-4,4a,5,6,7,8,8a,9-Octahydro-2H-pyrazolo[3,4-g] quinoline) methanol treated animals. Sulpiride dosages of 3, 10 and 30 mg/kg partially restored the inflammatory response in animals which received 10 mg/kg dosages of 7-(5-n-propyl-trans-4,4a,5,6,7,8,8a,9-octahydro-2H-pyrazolo[3,4-g] quinoline) methanol. See FIG. 9, Panel C.

Figure 10A:
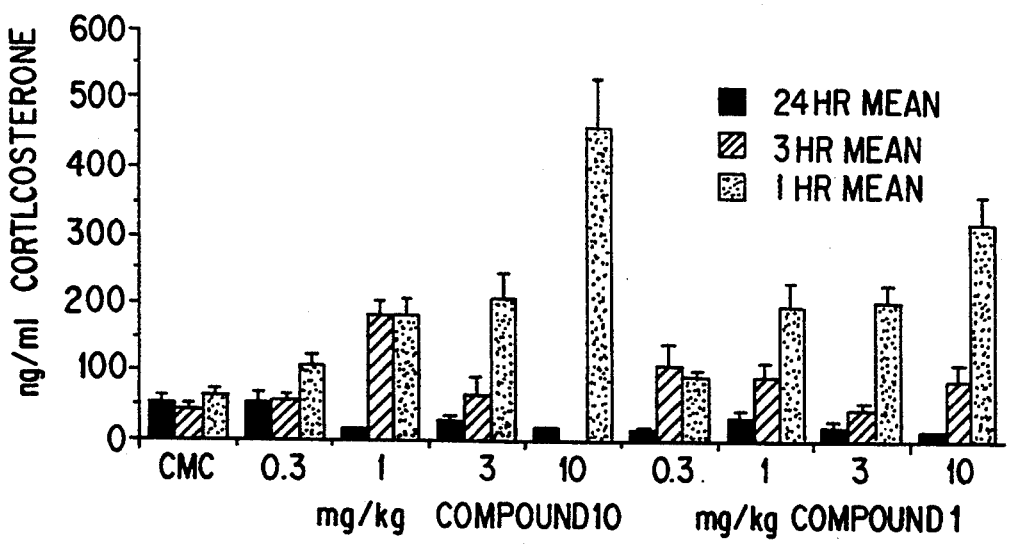
FIG. 10 Effect of compounds 10 and 1 on serum corticosterone levels in mice, at various time intervals following injection (panel A) and the inhibitory effect of compound 1 on the delayed type hypersensitivity (DTH) in adrenalectomized (ADX) mice (panel B). CMC= carboxymethylcellulose vehicle control; NEG=negative control for DTH; POS=positive control for DTH.

A further study attempting to elucidate the mechanism whereby ergolines exert anti-inflammatory activity is summarized in FIG. 10.

Figure 10B:
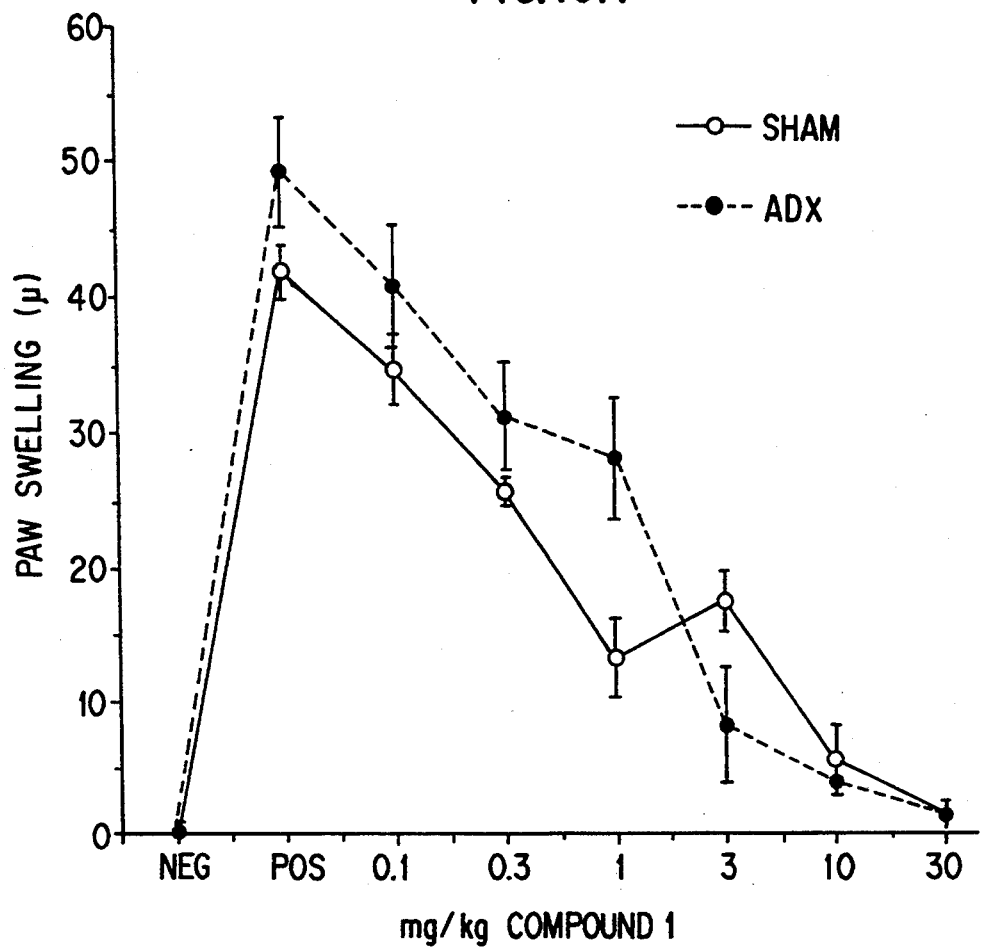

Dopamine agonists are known to elevate circulating glucocorticoid levels, via activation of the hypothalamo-pituitary-adrenal axis. The effect of example ergolines, 7-(5-n-propyl-trans-4,4a,5,6,7,8,8a, 9-octahydro-2H-pyrazolo[3,4-g] quinoline) methanol and D-1-isopropyl-6-n-propyl-8β-methylthiomethyl ergoline, on plasma corticosterone levels in mice is depicted in FIG. 10, Panel A. As can be seen, at 1 and 3 hr. intervals following injection these ergolines do increase plasma cortiosterone. Since glucocorticoids are potential endogenous anti-inflammatory substances, this action is one potential mechanism for the anti-inflammatory effect of the ergolines. However, in subsequent inflammation studies, the anti-inflammatory effects of D-1-isopropyl-6-n-propyl-8β-methylthiomethyl ergoline were retained in mice lacking an adrenal gland and therefore devoid of the increase in circulating corticosterone. (FIG. 10B)

Figure 11:
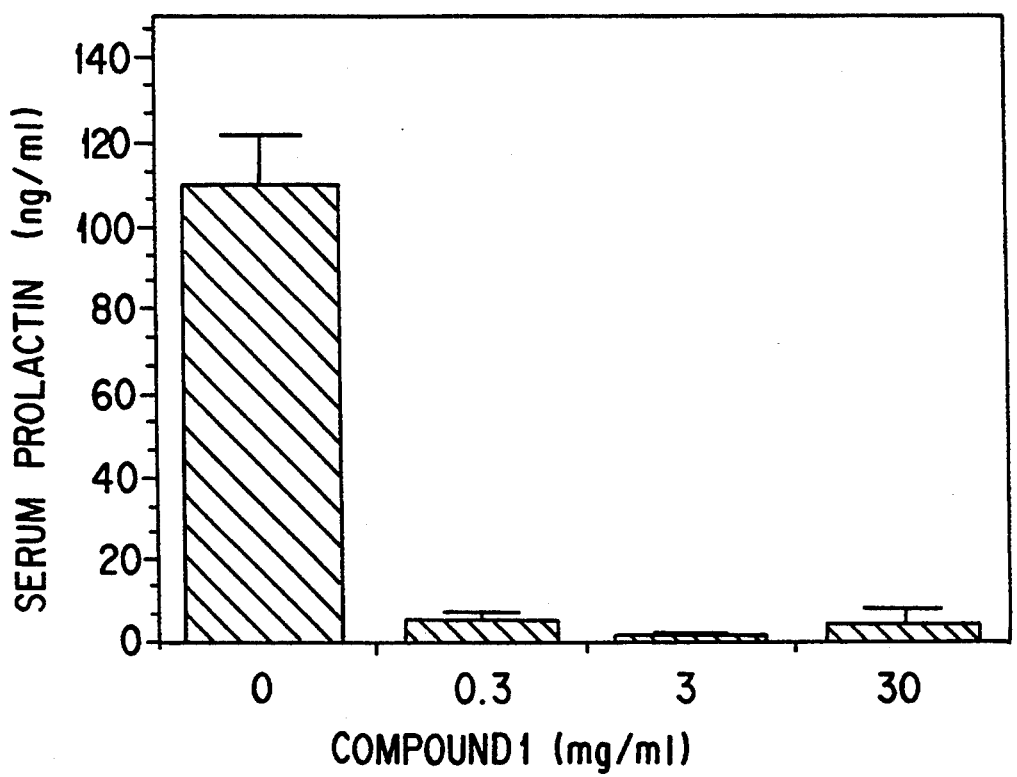
FIG. 11 Suppression of serum prolactin levels in rats by compound 1.
Figure 12:
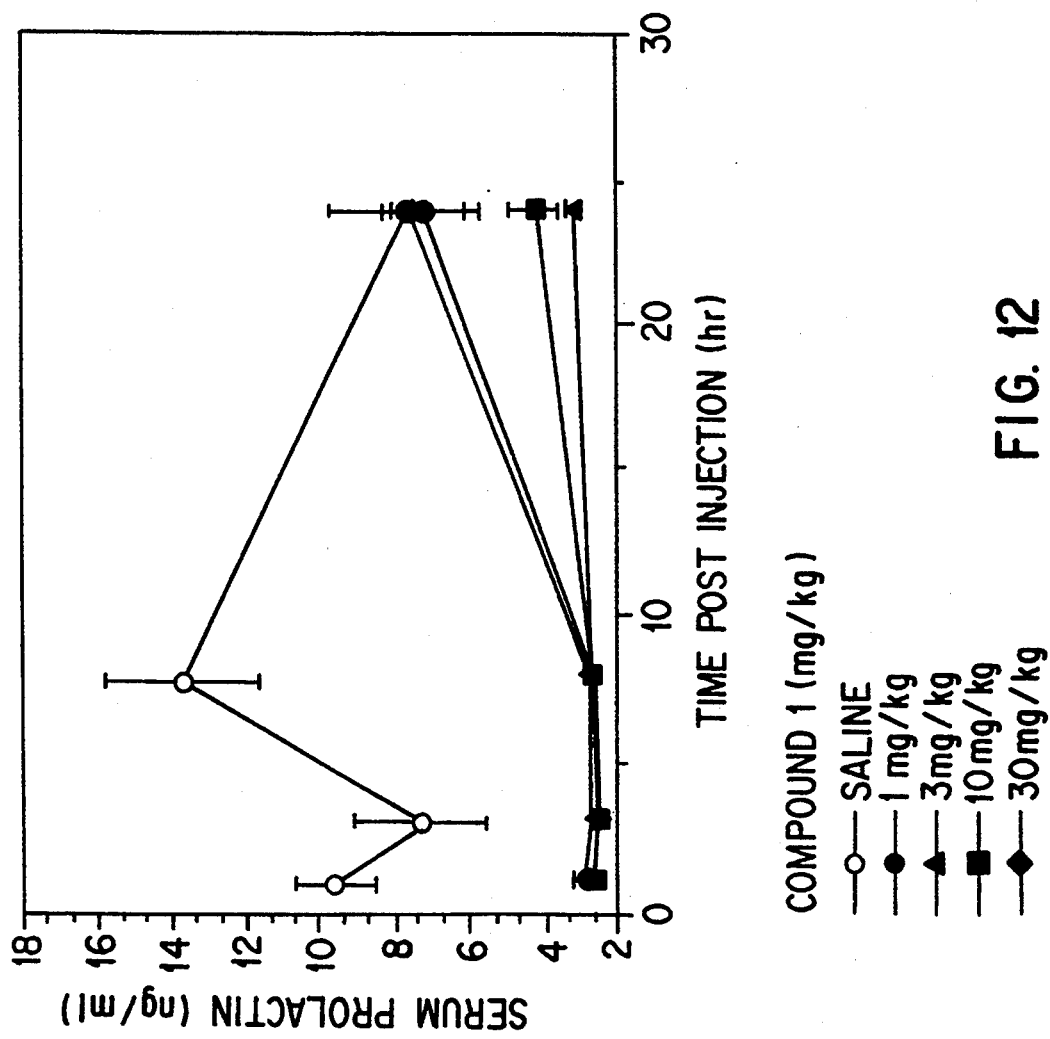
FIG. 12 Time course for suppression of serum prolactin in mice following a single injection of various doses of compound 1.

A further mechanistic study wherein rat serum prolactin levels were quantitated 1 hour post-treatment with varying doses of D-1-isopropyl-6-n-propyl-8β-methylthiomethyl ergoline is summarized in FIG. 11. The data of FIG. 11 reveals that D-1-isopropyl-6-n-propyl-8β-methylthiomethyl ergoline in the range of 0.3, 3 and 30 mg/kg dramatically reduced serum prolactin levels as determined by radio-immunoassay. A time course/dose response study of D-1-isopropyl-6-n-propyl-8β-methylthio-methyl ergoline effects on murine serum prolactin levels is presented in FIG. 12. Again, the particularly long lasting effects of this compound are noteworthy. There is however a disparity between the suppression of prolactin and anti-inflammatory activities of the ergolines with regard to the dose response profiles. Serum prolactin levels are much more sensitive to D-1-isopropyl-6-n-propyl-8β-methylthiomethyl ergoline (maximal suppression $\sim \leqq 0.1$ mg/kg) than are the anti-inflammatory effects 3–10 mg/kg, See FIG. 5).

Figure 13A:
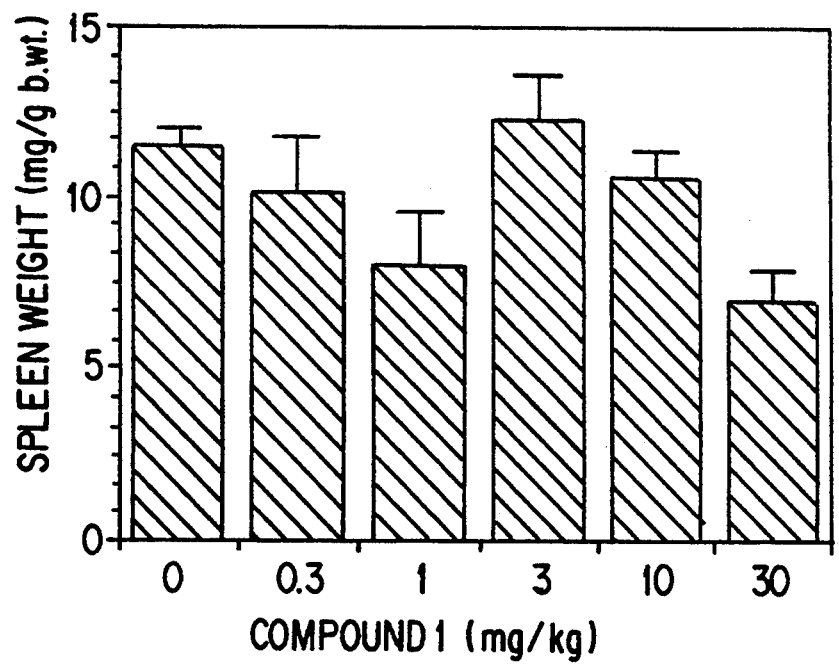
FIG. 13 Lack of effect of compounds 1 (panel A) and 5 (panel B) on splenomegaly in a muring graft vs host response (GVH). NEG=negative control for GVH; POS=positive control for GVH.
Figure 13B:
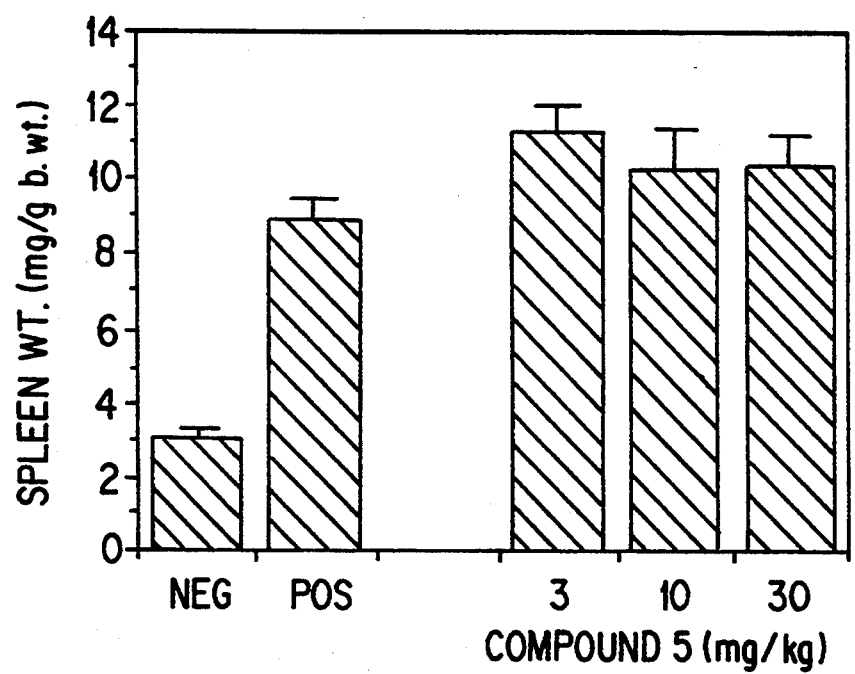

The absence of appreciable immunosuppressive activity of the ergoline compounds of the invention in a graft versus host model further substantiates the direct anti-inflammatory activity of the ergoline compounds of the invention. Experimental methodology used in the graft versus host (GVH) model is detailed in Example 2. The graft versus host model utilized in these studies consisted of injecting C57B16 murine spleen cells into B6C3F$_1$ mice (C57BL6/C3H/HEN). B6C3F$_1$ mice, which received C57BL6 spleen cells, were dosed with test compounds for 10 days. On day 10 the spleens were removed and weighed. An increase in spleen weight indicates immunological responsiveness. Compounds D-1-isopropyl-6-n-propyl-8β-methylthiomethyl ergoline and trans-($\pm$)-5-n-propyl-4,4a,5,6,7,8,8a,9-octahydro-1H-pyrazolo[3,4-g] quinoline displayed no immunosuppressive activity in this model. See FIG. 13. FIG. 13, illustrates the effect of spleen cell infusion across histocompatability (H-2) barriers. The negative control did not receive spleen cells and thus the spleen weight relative to total body weight is that of a healthy B6C3F$_1$ mouse.

In summary, the ergoline compounds described herein possess a unique anti-inflammatory activity devoid of typically immunosuppressive effects. Furthermore, the anti-inflamatory activities of the analogues of pergolide and quinpirole are separable from that ascribed previously to bromocriptine, which is most likely related to its immunosuppressive potential. The activity described in the acute paw swelling models is particularly conclusive, in that prototypical immunosuppressives are without effect in this model. Furthermore, classic immunologic responses (e.g. graft versus host response) were unaffected by D-1-isopropyl-6-n-propyl-8β-methyl-thiomethyl ergoline.

EXAMPLE 1

Delayed Type Hypersensitivity (DTH)

A. Animals

Male Balb/c mice (Charles River) weighing 20 to 25 g were used in all DTH studies. When adrenalectomized studies were carried out, sham surgery and adrenalectomized mice were obtained from the vendor. Animals were maintained on a 12:12 hour light:dark cycle. Mice were allowed ad lib access for food (Purina lab chow) and water (normal saline for adrenalectomized animals). Experimental groups consisted of 5 mice.

B. Protocol

A DTH response was assessed by measuring the degree of rear foot pad swelling induced by picryl chloride. On day 0, mice were sensitized with 100 μl of 5% picryl chloride (in ethanol), which was applied to a shaved abdomen. Negative control groups were shaved but not sensitized. On day 3, mice were anesthetized with methoxyflurane, and the baseline rear foot pad thickness was measured with a micrometer (Mitutoyo) in μ, and was recorded in duplicate. Fifty μl of picryl chloride was then applied to each pad with a pipet (Rainen) while the animal was unconscious. The negative controls also received picryl chloride at this point to control for primary irritancy. Twenty-four hours later, the mice were sacrificed by $CO_2$ asphyxiation and each rear foot pad was again measured in duplicate, and any evidence of foot pad swelling was calculated. The mean rear foot swelling change of both pads for each animal from days 3 to 4 was used as the index of immune function in the DTH assay.

This particular method of assessing a DTH response in mice is similar in part (antigen employed, tissue site measured) to previously published reports (e.g. Descotes, J and Evreux, J. C., Depressant effects of major tranquilizers on contact hypersensitivity to picryl chloride in the mouse, *Experientia* 37:1004–1005 (1981); Descotes, J., Tedone, R. and Evreus, J. C., Different effects of psychotropic drugs on delayed hypersensitivity responses in mice, *J. Neuroimmuno.* 9:81–85 (1985). However, this particular method differs from other methods reported in the literature, in that this method involves a five day schedule, whereas other reports typically employ a seven day schedule.

C. Dosing

Unless otherwise stated all animals were given four subcutaneous doses of test compound just prior to picryl chloride sensitization on day 0, on day 1 and day 2, and just prior to picryl chloride challenge on day 3. In a few experiments, compounds were administered via oral or intraperitoneal routes. All drugs were delivered as suspensions in 1% carboxy-methylcellulose (also contained 0.8% NaCl, 1% polysorbate-80, 1.4% benzyl alcohol). Carboxymethyl-cellulose (1%) was used in control injections.

EXAMPLE 2

Graft Verses Host Response (GVH)

A. Animals

Male B6C3F1 and C57BL mice (Charles River) weighing 20 to 25 g were used in all GVH studies. Animals were maintained on a 12:12 hour light:dark cycle. Mice were allowed ad lib access for food (Purina lab chow) and water. Experimental groups consisted of 5 mice.

B. Protocol

The GVH response was assessed by measuring the degree of splenomegaly induced by the injection of F$_1$ hybrid mice with splenocytes obtained from one of the parental strains. With this experimental design, the immune system of the hybrid (host) does not recognize the injected parental spleen cells (graft) as foreign while the injected cells mount an immune response towards the host, resulting in splenomegaly. C57/BL mice were used as the parental strain, and B6C3F$_1$ mice as the host. Spleen cells of C57/BL mice were removed and placed in Hank's balanced salt solution (HBSS; Sigma Chemical Co., St. Louis, Mo.), containing 20 mM 4-(2-hydroxyethyl)-1-piperazineethanesulfonic acid buffer (Gibco Laboratories, Grand Island, N.Y.), 0.1 unit/ml penicillin and 1 μg/ml streptomycin (Gibco). Spleen cells were dissociated in stainless steel mesh screens, lysed with ammonium chloride buffer (0.012M Tris and 0.14M NH$_4$Cl), and washed twice in the modified HBSS. Cells were diluted to $2 \times 10^8$ cells/ml and were injected i.p. in a volume of 0.5 ml/mouse on day 0. Negative control groups received either HBSS. We have demonstrated in our model that utilization of HBSS as the negative control is equivalent to the use of B6C3F$_1$ spleen cell injections (prepared as described above) on day 0 (Bryant, H. U. and Roudebush, R. E., Suppressive effects of morphine pellet implants on in vivo parameters of immune function, *J. Pharmacol. Exp. Ther.*, (in press)).

On day 10, the hybrid mice were sacrificed by carbon dioxide asphyxiation and the spleens were removed and weighed. The ratio of spleen weight to body weight, a very reliable indicator of the GVH response (Simonsen, M., Graft versus host reactions. Their natural history, and applicability as tools of research, *Prog. Allergy* 6:349–467 (1962), was used as the index of immune function in the GVH assay.

C. Dosing

All animals were given ten subcutaneous doses of test compound, administered daily. All drugs were delivered as suspensions in 1% carboxymethylcellulose which served as the control injection.

EXAMPLE 3

Acute Inflammatory Responses

A. Animals

Male Lewis rats (Charles River or Harlan Sprague Dawley) weighing 180 to 250 g were used in all acute inflammatory studies. Animals were maintained on a 12:12 hour light:dark cycle and were allowed ad lib access for food (Purina lab chow) and water. Experimental groups consisted of 5 or 6 rats.

B. Protocol

Acute paw swelling was induced by the intraplantar injection of phlogistic agents into the left hind paw, with the uninjected right hind paw serving as the comparative control. One hour after dosing with test compound, 50 μl of serotonin (Sigma; 0.005 to 0.2 mg/ml in normal saline) or substance P (Sigma; 0.01 or 0.05 mg/ml in 10% thiorphan in normal saline) or carrageenan (Marine Colloidal or Sigma Type IV; 1% in normal saline) were injected under the skin of the left hind paw, while the animal was restrained in a plastic cone. Negative controls were given 50 μl intradermal injections of normal saline (serotonin or carrageenan assays) or 10% thiorphan (substance P assays) into the left hind paw. One hour following injection of serotonin, or 30 minutes following injection of substance P, or 180 minutes following injection of carrageenan, the animals were sacrificed by $CO_2$ asphyxiation. The right and left hind paws were cut just proximal to the tibiotarsal joint and weighed. The difference in weight between an individual animal's left and right paws were used as an indicator of tissue swelling.

C. Dosing

As indicated above, test compounds are administered as a one hour pretreatment. In one series of experiments, 24 hour and 48 hour drug pretreatment periods were used. Test compounds were dosed intraperitoneally as a suspension in 1% carboxymethylcellulose.

EXAMPLE 4

Neuroendocrine Paramaters

A. Animals

Both Balb/C mice (male, approximately 20 g, Charles Rivers) and Lewis rats (male, approximately 200 g, Charles River or Harlan Sprague Dawley) were used in neuroendocrine studies. Animals were maintained on a 12:12 hour light:dark cycle and were allowed ad lib access for food (Purina lab chow) and water. Experimental groups consisted of 6 to 8 animals.

B. Protocol

After dosing with test compounds, animals were sacrificed by decapitation at 1, 3, 8 or 24 hour intervals. Trunk blood was collected, allowed to clot and serum obtained after centrifugation (3000 rpm for 15 min.). Serum was aliquoted and stored at −70° C. for subsequent radioimmunoassays. Serum prolactin was determined by radioimmunoassay. Serum corticosterone levels were determined with a kit designed for such determinations and obtained from ICN.

Statistical Analyses

Every experiment consisted of negative controls, positive controls and drug treated groups. Within individual experiments groups were initially compared with a one-way analysis of variance and post-hoc range testing (Scheffe F-test) when statistical significance was indicated ($p<0.05$). The statistical package utilized was Statview 512+ (BrainPower Inc.).

We claim:

1. A method of treating inflammation in a mammal having inflammation in the substantial absence of immunosuppression consisting essentially of administering to said mammal an effective amount of a compound having the formula

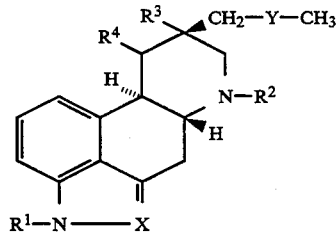

where

X is CH or N;

Y is O or S;

$R^1$ is 2-propenyl, $C_1$–$C_3$ alkyl, benzyl or substituted benzyl where the substituents are one or two of the same or different selected from methyl, ethyl, methoxy, ethoxy, hydroxy, chloro, bromo and fluoro;

$R^2$ is $C_2$–$C_3$ alkyl allyl or cyclopropylmethyl;

$R^3$ and $R^4$ are both hydrogen or combine to form a carbon-carbon bond; or the formula

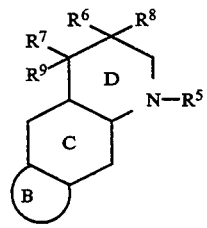

IB wherein the C and D rings are trans fused;

$R^5$ is ($C_2$–$C_3$) alkyl, allyl, or cyclopropylmethyl;

$R^6$ is hydrogen, $CH_2OH$, $CH_2OCH_3$, $CH_2SCH_3$, $CH_2SOCH_3$ or $CH_2SO_2CH_3$;

$R^7$ is hydrogen or OH;

$R^8$ and $R^9$ are both hydrogen, or combine to form a carbon-carbon bond provided that when $R^7$ is OH, $C^8$ and $C^9$ are H; and represents (a) [pyrazole structure with N, HN]

(b) [pyrazole structure with HN, N]

(c) [pyrimidine structure with N, N, $NR^{10}R^{11}$]

(d) [pyridine structure with N, $R^{10}R^{11}N$]

or (e) [thiazole structure with N, S, $R^{10}R^{11}N$]

where
$R^{10}$ and $R^{11}$ are individually hydrogen or $C_1$–$C_3$ alkyl or benzyl; or pharmaceutically acceptable acid addition salt thereof.

2. The method of claim 1 wherein said mammal is a human.

3. The method of claim 2 where said compound has the formula

[structure with $R^3$, $R^4$, $CH_2$—Y—$CH_3$, H, N—$R^2$, H, $R^1$—N——X]

where
X is CH or N;
Y is O or S;
$R^1$ is 2-propenyl, $C_1$–$C_3$ alkyl, benzyl or substituted benzyl where the substituents are one or two of the same or different selected from methyl, ethyl, methoxy, ethoxy, hydroxy, chloro, bromo and fluoro;
$R^2$ is $C_2$–$C_3$ alkyl, allyl or cyclopropylmethyl;
$R^3$ and $R^4$ are both hydrogen or combine to form a carbon-carbon bond; or a pharmaceutically acceptable acid addition salt thereof.

4. The method of claim 3 where
X is CH;
Y is S;
$R^1$ is hydrogen or isopropyl;
$R^2$ is n-propyl;
$R^3$ and $R^4$ are both hydrogen; or a pharmaceutically acceptable acid addition salt thereof.

5. The method of claim 4 where the compound is 1-isopropyl-6-n-propyl-8β-methylthiomethylergoline or a pharmaceutically acceptable acid addition salt thereof.

6. The method of claim 2 where said compound has the formula

[structure with $R^6$, $R^7$, $R^8$, $R^9$, D, N—$R^5$, C, B]

wherein
the C and D rings are trans fused;
$R^5$ is ($C_2$–$C_3$)alkyl, allyl, or cyclopropylmethyl;
$R^6$ is hydrogen, $CH_2OH$, $CH_2OCH_3$, $CH_2SCH_3$, $CH_2SOCH_3$ or $CH_2SO_2CH_3$;
$R^7$ is hydrogen or OH;
$R^8$ and $R^9$ are both hydrogen, or combine to form a carbon-carbon bond provided that when $R^7$ is OH, $C^8$ and $C^9$ are H; and represents (a) [pyrazole structure with N, HN]

(b) [pyrazole structure with HN, N]

(c) [pyrimidine structure with N, N, $NR^{10}R^{11}$]

-continued (d) 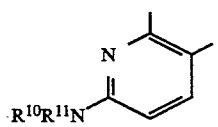

or (e) 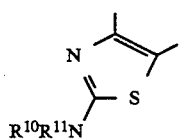

where
R$^{10}$ and R$^{11}$ are individually hydrogen or C$_2$–C$_3$ alkyl or benzyl; or pharmaceutically acceptable acid addition salt thereof.

7. The method of claim 6 where
R$^5$ is n-propyl;
R$^6$ is hydrogen or CH$_2$OH
R$^7$ is hydrogen
R$^8$ and R$^9$ are both hydrogen or combine to form a carbon-carbon-bond; and

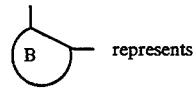 represents

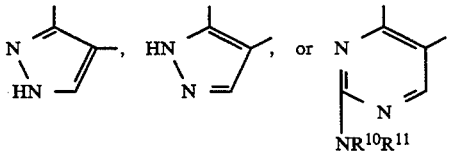

represents
where
R$^{10}$ and R$^{11}$ are both hydrogen; or a pharmaceutically acceptable salt thereof.

* * * * *

UNITED STATES PATENT AND TRADEMARK OFFICE
CERTIFICATE OF CORRECTION

PATENT NO. : 5,416,090

DATED : May 16, 1995

INVENTOR(S) : Alison M. Bendele, Henry U. Bryant and John M. Schaus

It is certified that error appears in the above-indentified patent and that said Letters Patent is hereby corrected as shown below:

Claim 6, line 23, which is Column 21, line 19, "$C_2-C_3$" should read -- $C_1-C_3$ --.

Claim 7, line 9, which is Column 22, line 19, delete the word "represents".

Signed and Sealed this

Twenty-fourth Day of October, 1995

Attest:

BRUCE LEHMAN

Attesting Officer

Commissioner of Patents and Trademarks